US012056877B2

United States Patent
He et al.

(10) Patent No.: US 12,056,877 B2
(45) Date of Patent: Aug. 6, 2024

(54) NEURAL-NETWORK-DRIVEN TOPOLOGY FOR OPTICAL COHERENCE TOMOGRAPHY SEGMENTATION

(71) Applicant: The Johns Hopkins University, Baltimore, MD (US)

(72) Inventors: Yufan He, Baltimore, MD (US); Jerry L. Prince, Baltimore, MD (US); Aaron Carass, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 378 days.

(21) Appl. No.: 17/594,191

(22) PCT Filed: Mar. 25, 2020

(86) PCT No.: PCT/US2020/024622
§ 371 (c)(1),
(2) Date: Oct. 6, 2021

(87) PCT Pub. No.: WO2020/210028
PCT Pub. Date: Oct. 15, 2020

(65) Prior Publication Data
US 2022/0156941 A1 May 19, 2022

Related U.S. Application Data

(60) Provisional application No. 62/831,014, filed on Apr. 8, 2019.

(51) Int. Cl.
*G06K 9/00* (2022.01)
*A61B 3/00* (2006.01)
(Continued)

(52) U.S. Cl.
CPC .............. *G06T 7/11* (2017.01); *A61B 3/0025* (2013.01); *A61B 3/0058* (2013.01);
(Continued)

(58) Field of Classification Search
CPC . G06T 7/11; G06T 7/0012; G06T 7/12; G06T 7/143; G06T 7/73;
(Continued)

(56) References Cited

U.S. PATENT DOCUMENTS 8,571,278 B2 * 10/2013 Sonka ....................... G06T 7/11
382/128
10,055,851 B2 * 8/2018 Spector ..................... G06T 7/12
(Continued)

FOREIGN PATENT DOCUMENTS

WO     2018209438 A1     11/2018

OTHER PUBLICATIONS

Fang et al., "Automatic segmentation of nine retinal layer boundaries in OCT images of non-exudative AMD patients using deep learning and graph search," Biomedical Optics Express, vol. 8, No. 5, May 2017, 13 Pages.
(Continued)

*Primary Examiner* — Shervin K Nakhjavan
(74) *Attorney, Agent, or Firm* — Harrity & Harrity, LLP

(57) ABSTRACT

A device receives a two-dimensional (2-D) image that depicts a cross-sectional view of a macula comprised of layers and boundaries to segment the layers, and determines spatial coordinates of the 2-D image that include x-coordinates and y-coordinates. The device uses a data model, that has been trained using a deep learning technique, to process the 2-D image and the spatial coordinates to generate boundary maps that indicate likelihoods of voxels of the 2-D image being in positions that are part of particular boundaries. The device determines, by analyzing the boundary maps, an initial set of boundary positions, and determines a final set of boundary positions by using a topological order identification technique to refine the initial set of boundary positions. The device determines the thickness levels of the
(Continued)

layers of the macula based on the final set of boundary positions, and performs one or more actions based on the thickness levels.

20 Claims, 12 Drawing Sheets

(51) Int. Cl.
*A61B 3/10* (2006.01)
*A61B 3/12* (2006.01)
*G06N 3/08* (2023.01)
*G06T 7/00* (2017.01)
*G06T 7/11* (2017.01)
*G06T 7/12* (2017.01)
*G06T 7/143* (2017.01)
*G06T 7/73* (2017.01)
*G16H 20/10* (2018.01)
*G16H 70/60* (2018.01)

(52) U.S. Cl.
CPC .............. *A61B 3/1005* (2013.01); *A61B 3/12* (2013.01); *G06N 3/08* (2013.01); *G06T 7/0012* (2013.01); *G06T 7/12* (2017.01); *G06T 7/143* (2017.01); *G06T 7/73* (2017.01); *G16H 20/10* (2018.01); *G16H 70/60* (2018.01); *G06T 2207/10101* (2013.01); *G06T 2207/20076* (2013.01); *G06T 2207/20081* (2013.01); *G06T 2207/20084* (2013.01); *G06T 2207/30041* (2013.01)

(58) Field of Classification Search
CPC . G06T 2207/10101; G06T 2207/20076; G06T 2207/20081; G06T 2207/20084; G06T 2207/30041; A61B 3/0025; A61B 3/0058; A61B 3/1005; A61B 3/12; A61B 3/102; A61B 3/1225; G06N 3/08; G06N 3/045; G16H 20/10; G16H 70/60
See application file for complete search history.

(56) References Cited

U.S. PATENT DOCUMENTS

| | | | | |
|---|---|---|---|---|
| 10,803,592 | B2* | 10/2020 | Grady | G06T 7/0012 |
| 11,122,981 | B2* | 9/2021 | Olender | A61B 5/0035 |
| 11,288,813 | B2* | 3/2022 | Grady | G06T 7/149 |
| 11,302,043 | B2* | 4/2022 | Camino | G06T 5/008 |
| 2018/0047159 | A1* | 2/2018 | Schlegl | G06N 3/04 |
| 2019/0043193 | A1 | 2/2019 | Odaibo et al. | |
| 2021/0319556 | A1* | 10/2021 | Chauhan | G06T 7/12 |

OTHER PUBLICATIONS

He et al., "Topology guaranteed segmentation of the human retina from OCT using convolutional neural networks," Website: https://arxiv.org/abs/1803.05120, Mar. 14, 2018, 9 Pages.

International Search Report and Written Opinion—PCT/2020/024622—ISA/KR—Jul. 9, 2020.

Extended European Search Report for Application No. EP20788428.9 mailed on Dec. 6, 2022, 9 pages.

He et al., "Towards Topological Correct Segmentation of Macular OCT from Cascaded FCNs," Sep. 2017, SAT 2015 18th International Conference, Sep. 24-27, 2015; [Lecture Notes in Computer Science; Lect.notes Computer], Springer, Berlin, Heidelberg, pp. 202-209, XP047439812, ISBN: 978-3-540-7 4549-5 [retrieved on Sep. 9, 2017].

Hiroshi et al., "Macular Segmentation With Optical Coherence Tomography," Investigative Ophthalmology & Visual Science, Association for Research in Vision and Ophthalmology, US, Jun. 2005, vol. 46(6), pp. 2012-2017, XP002408330, ISSN: 0146-0404, DOI: 10.1167/IOVS.04-0335.

* cited by examiner

| Macula Layers |
|---|
| • Retinal Nerve Fiber (RNFL) |
| • Ganglion Cell and Inner Plexiform Complex (GCIP) |
| • Inner Nuclear Layer (INL) |
| • Outer Plexiform Layer (OPL) |
| • Outer Nuclear Layer (ONL) |
| • Inner Segment (IS) |
| • Outer Segment (OS) |
| • Retinal Pigment Epithelium (RPE) |

| Macula Boundaries |
|---|
| • Vitreous-RNFL or Internal Limiting Membrane (ILM) |
| • RNFL-GCIP |
| • GCIP-INL |
| • INL-OPL |
| • OPL-ONL |
| • ONL-IS |
| • IS-OS (i.e., Ellipsoid Zone (EZ)) |
| • OS-RPE |
| • RPE-Choroid or Bruch's Membrane (BM) |

| Training Data |
|---|
| • Labeled set of images that identify boundaries and layers of maculae of human eyes |

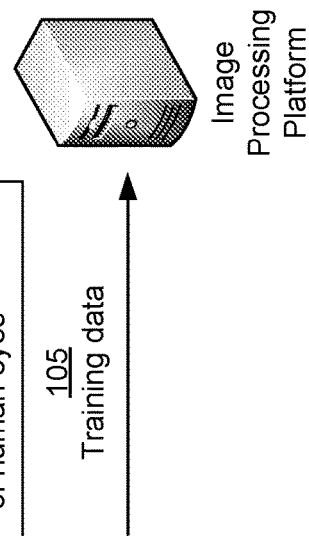

105
Training data

Image Processing Platform

125
Capture Set of B-scans of a Macula of a Patient

130
B-scans

135
Pre-processing Operations

Image Processing Platform

145
Determine initial boundary positions by using a soft argmax function of the data model to analyze boundary maps Image Processing Platform

NEURAL-NETWORK-DRIVEN TOPOLOGY FOR OPTICAL COHERENCE TOMOGRAPHY SEGMENTATION

RELATED APPLICATIONS

This application is a 371 national stage of PCT Application PCT/US2020/024622 filed on Mar. 25, 2020, entitled "A NEURAL-NETWORK-DRIVEN TOPOLOGY FOR OPTICAL COHERENCE TOMOGRAPHY SEGMENTATION," which claims priority to U.S. Provisional Patent Application No. 62/831,014, filed on Apr. 8, 2019, both of which are hereby expressly incorporated by reference herein.

This invention was made with Government support under grant EY024655, awarded by the National Institutes of Health (NIH). The Government has certain rights in the invention.

BACKGROUND

Optical coherence tomography (OCT) is used to produce high resolution depth images of the retina and is now the standard of care for in-vivo ophthalmological assessment. Additionally, OCT is used for evaluation of neurological disorders, such as multiple sclerosis (MS).

SUMMARY

According to some implementations, a method may include receiving, by a device, a two-dimensional (2-D) image that depicts a cross-sectional view of a retina of an eye, wherein the retina includes a macula that includes layers and boundaries that are used to segment the layers. The method may include converting, by the device, the 2-D image to a standardized format, and determining, by the device, a set of spatial coordinates of the 2-D image that is in the standardized format, wherein the set of spatial coordinates include: a set of x-coordinates, and a set of y-coordinates. The method may include generating, by the device and by using a data model to process the 2-D image and the set of spatial coordinates, a set of boundary maps that indicate likelihoods of voxels of the 2-D image being in positions that are part of particular boundaries, wherein the data model has been trained using a deep-learning technique, and wherein a likelihood that a voxel, of the voxels of the 2-D image, is in a position that part of a particular boundary is relative to other voxels, of the voxels of the 2-D image, that share a y-coordinate of the set of y-coordinates with the voxel of the voxels. The method may include determining, by the device and by using the data model to analyze the set of boundary maps, an initial set of boundary positions for the boundaries, determining, by the device, a final set of boundary positions by using a topological order identification technique of the data model to refine the initial set of boundary positions, and providing, by the device, data that identifies the final set of boundary positions for display via an interface.

According to some implementations, a device may include one or more memories, and one or more processors, operatively coupled to the one or more memories, to identify a data model that is trained using deep learning to determine likelihoods of particular voxels being within a layer of a particular macula. The one or more processors may receive a 2-D image that depicts a cross-sectional view of a macula of an eye, wherein the macula includes: layers, and boundaries to segment the layers. The one or more processors may determine a set of spatial coordinates of the 2-D image, wherein the set of spatial coordinates include: a set of x-coordinates, and a set of y-coordinates. The one or more processors may generate, by using the data model to process the 2-D image and the set of spatial coordinates, a set of boundary maps that indicate likelihoods of voxels of the 2-D image being in positions that are part of particular boundaries, wherein a likelihood that a voxel, of the voxels of the 2-D image, is in a position part of a particular boundary is relative to other voxels, of the voxels of the 2-D image, that share a y-coordinate of the set of y-coordinates with the voxel. The one or more processors may determine, by using the data model to analyze the set of boundary maps, an initial set of boundary positions for the boundaries, and determine a final set of boundary positions by using a topological order identification technique of the data model to refine the initial set of boundary positions. The one or more processors may determine, after determining the final set of boundary positions, thickness levels of the layers of the macula based on the final set of boundary positions, determine whether the thickness levels of the layers are indicative of a disease, and perform one or more actions based on determining whether the thickness levels of the layers are indicative of the disease.

According to some implementations, a non-transitory computer-readable medium may store one or more instructions that, when executed by one or more processors of a device, cause the one or more processors to receive a 2-D image that depicts a cross-sectional view of a retina of an eye, wherein the retina includes a macula that includes: layers, and boundaries to segment the layers. The one or more instructions may cause the one or more processors to convert the 2-D image to a standardized format, and determine a set of spatial coordinates of the 2-D image that has been converted to the standardized format, wherein the set of spatial coordinates include: a set of x-coordinates, and a set of y-coordinates. The one or more instructions may cause the one or more processors to use a data model to process the 2-D image and the set of spatial coordinates to: generate a set of boundary maps that indicate likelihoods of voxels of the 2-D image being in positions that are part of particular boundaries, wherein the data model has been trained using a deep learning technique. The one or more instructions may cause the one or more processors to determine, by analyzing the set of boundary maps, an initial set of boundary positions for the boundaries. The one or more instructions may cause the one or more processors to determine a final set of boundary positions for the boundaries by using a topological order identification technique to refine the initial set of boundary positions. The one or more instructions may cause the one or more processors to determine, after determining the final set of boundary positions, thickness levels of the layers of the macula based on the final set of boundary positions, and perform one or more actions based on the thickness levels of the layers of the macula.

BRIEF DESCRIPTION OF THE DRAWINGS

FIGS. 1A-1G are diagrams of one or more example implementations described herein.

DETAILED DESCRIPTION

Figure 1B:
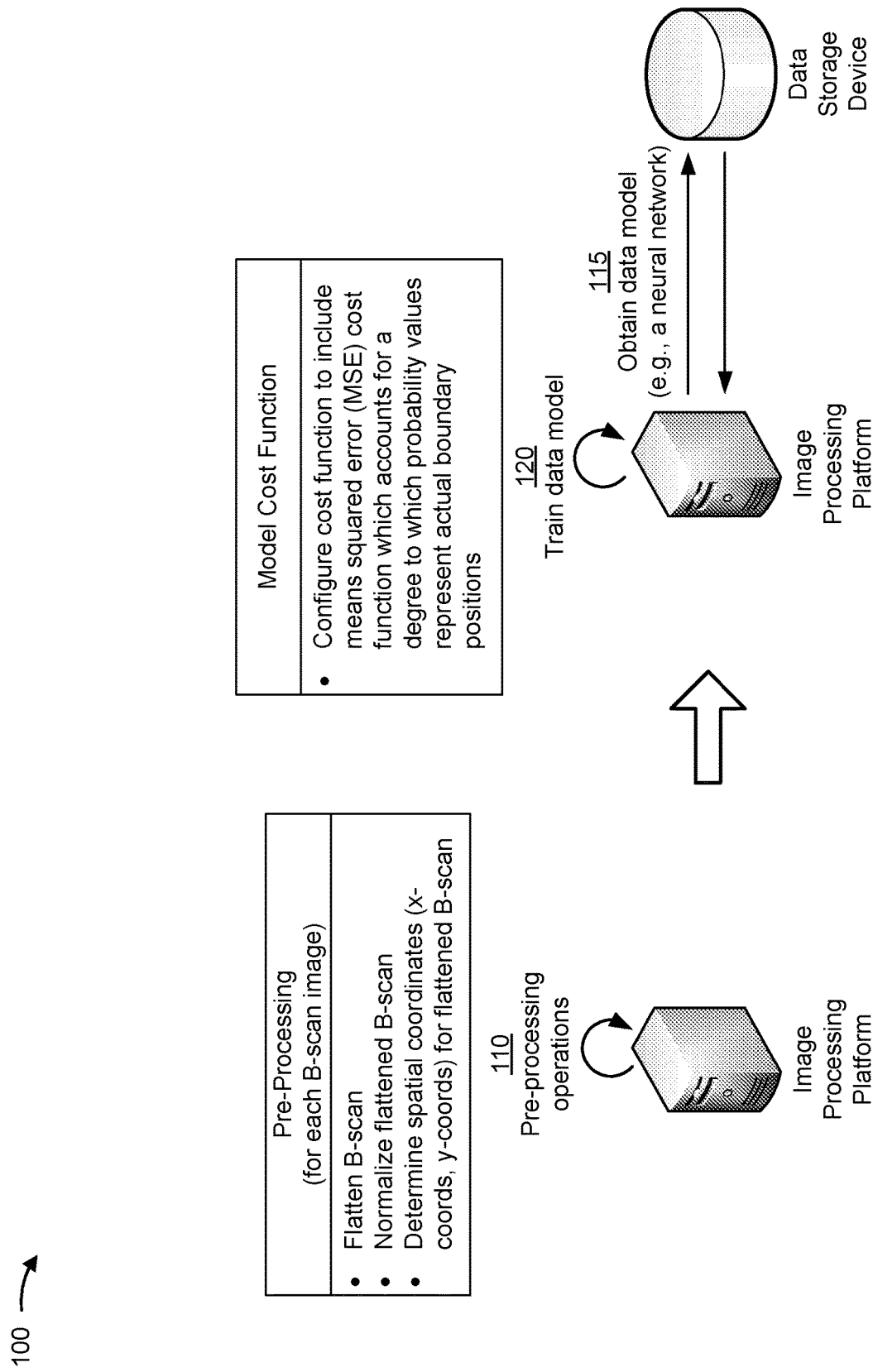

The following detailed description of example implementations refers to the accompanying drawings. The same reference numbers in different drawings may identify the same or similar elements.

Optical coherence tomography (OCT) may be used for evaluation of retinal and neurological disorders, such as multiple sclerosis (MS). For example, to determine whether a patient has MS, an ophthalmological assessment may be performed that determines whether MS is present based on a thickness of a set of cellular layers (referred to herein as layers) of a macula of the patent's eye. The thickness may serve as an indicator of whether the patient has MS, because an individual with MS may have reduced thickness at one or more layers of the macula (relative to a healthy patient). Additionally, or alternatively, the thickness may serve as an indicator of whether the patient's treatment has been working (e.g., by slowing a gradual thinning of particular layers of the macula).

To measure the thickness, an imaging system may be used to capture images of the eye. In this case, the imaging system may emit a beam of light into tissues of the eye and may detect reflected or back-scattered light from the tissues. This reflected light will interfere with light that originated from the same source and may be used to generate a collection of amplitude scans (A-scans). The A-scans may be combined to form 2-D brightness-mode scans (B-scans) that are collectively referred to as a three-dimensional (3-D) OCT volume.

Several techniques exist for identifying the thickness of the set of layers of the macula. For example, manual segmentation involves having a team of human experts analyze the OCT volume to manually identify boundaries of the set of layers of the macula. This solution is time consuming and subjective. A number of other techniques involve automatic segmentation, whereby software is able to identify the boundaries of the set of layers of the macula. For example, some automatic segmentation techniques may generate models based on shortest paths, active contours, level sets, and the like.

However, many of these automatic segmentation techniques are unable to achieve a sub-voxel level of accuracy when identifying the layers. Because of the level of granularity that goes into identifying boundaries of a layer of a macula, even slightly inaccurate identifications of the boundaries may lead to inaccurate test results (e.g., a test result indicating that the patient has a thinning macula when the macula is in fact stable). Furthermore, some automatic segmentation techniques rely on a voxel-driven labeling scheme that inefficiently classifies each voxel in an OCT volume into layers or boundaries. However, automatic segmentation techniques that rely on the voxel-driven labeling scheme will be unable to guarantee that an appropriate layer topology is maintained. This causes a device implementing the automatic segmentation techniques to waste resources processing the OCT volume in a manner that generates inaccurate boundary positions.

Some implementations described herein provide an image processing platform to use a data model to determine boundary positions for boundaries used to segment a set of layers of a macula, where the boundary positions are determined with sub-voxel precision and in a manner that preserves an appropriate layer topology. For example, an imaging system may capture a set of 2-D images (e.g., B-scans) of the macula and may provide the set of 2-D images to the image processing platform. In this case, the image processing platform may convert the 2-D images to a standardized format and may determine a set of features for voxels included in the 2-D images.

Additionally, the image processing platform may determine or identify a set of spatial coordinates that are to be applied to the set of 2-D images. The set of spatial coordinates may include a set of x-coordinates and a set of y-coordinates. In this case, the image processing platform may generate a set of boundary maps that indicate likelihoods of the voxels being part of particular boundaries. For example, the image processing platform may have trained a data model using a deep-learning technique and may generate the set of boundary maps by using the data model to process the 2-D images that have been converted to the standardized format. The likelihoods of the voxels being part of particular boundaries may be relative to other voxels that share a y-coordinate (e.g., such that a group of voxels that share a y-coordinate will have likelihoods that add up to one, thereby ensuring that only one voxel per y-coordinate may be identified as being part of a given boundary).

Furthermore, the image processing platform may use the set of boundary maps to determine an initial set of boundary positions for the boundaries and may determine a final set of boundary positions by using a topological order identification technique of the data model to refine the initial set of boundary positions. The final set of boundary positions may identify positions within B-scans that collectively represent the boundaries of the set of layers, while preserving the appropriate layer topology. In this case, the image processing platform may provide data that identifies the final set of boundary positions for display via an interface. This may allow a doctor to view the final set of boundaries, measure thickness of each layer, and make a determination regarding the thickness, such as determining whether a patient has a neurological disorder (e.g., MS, etc.), determining a degree to which the neurological disorder has advanced or accelerated over time, determining an effectiveness of treatment being administered to the patient, and/or the like.

In this way, the image processing platform is able to accurately identify the boundaries that segment the set of layers of the macula with voxel or sub-voxel accuracy and in a manner that preserves the appropriate layer topology. Furthermore, the image processing platform is able to identify the boundaries while making an efficient and effective use of resources (e.g., processing resources, network resources, and/or the like). For example, by identifying the boundaries using a fully convolutional neural network that uses a single feed forward propagation (e.g., without any fully connected layers), the image processing platform reduces a utilization of resources relative to one or more inferior techniques that have to implement more extensive model training procedures (e.g., that process large numbers of parameters, that waste memory resources when utilizing the fully connected layers, etc.), reduces a utilization of processing relative to one or more inferior techniques that use multiple data models or networks, and/or the like. Moreover, by identifying boundary positions with voxel or sub-voxel precision, the image processing platform improves accuracy of test results, thereby conserving resources that might otherwise be used to generate and/or correct inaccurate test results.

FIGS. 1A-1G are diagrams of one or more example implementations 100 described herein. Example implementation(s) 100 may include an image processing platform, a data storage device, an imaging system, and a user device. As shown in FIGS. 1A-1G, the image processing platform may use a data model to determine boundary positions for boundaries used to segment layers of a macula of a patient and to use data that identifies the boundaries to determine whether a patient has an eye disorder or a neurological disorder, such as multiple sclerosis (MS).

As shown in FIG. 1A, and by reference number 105, the image processing platform may receive training data that that may be used to train the data model. For example, the image processing platform may receive training data that includes a labeled set of images of maculae of human eyes. The labeled set of images may include data that identifies a set of layers of the maculae and data that identifies boundaries that are used to segment the set of layers.

As shown, the set of layers may include a retinal nerve fiber (RNFL) layer, a ganglion cell and inner plexiform complex (GCIP) layer, an inner nuclear layer (INL), an outer nuclear layer (ONL), an inner segment (IS) layer, an outer segment (OS) layer, and a retinal pigment epithelium (RPE) layer. The set of boundaries may be used to define the layers (e.g., by identifying a line that separates two neighboring layers). The set of boundaries may include a vitreous-RNFL or internal limiting membrane (ILM) boundary, an RNFL-GCIP boundary, a GCIP-INL boundary, an INL-OPL boundary, an OPL-ONL boundary, an ONL-IS boundary, an OS-RPE boundary, and an RPE-Choroid or Bruch's membrane (BM) boundary.

In this way, the image processing platform receives training data that may be used to train the data model.

As shown in FIG. 1B, and by reference number 110, the image processing platform may perform one or more pre-processing operations to convert the training data to a standardized format. For example, the image processing platform may flatten the set of B-scans, may normalize the set of B-scans that have been flattened, and may determine or identify set of spatial coordinates for the set of B-scans that have been flattened. This will allow the image processing platform to train the data model using images that share a common format, file type, and/or the like.

In some implementations, the image processing platform may flatten a B-scan. For example, the image processing platform may analyze the B-scan to estimate positions (i.e., locations within the B-scan) of outer-most boundaries of the set of layers (e.g., the ILM and the BM). In this case, the image processing platform may filter the B-scan using a Gaussian smoothing technique. For example, the image processing platform may use a configured Gaussian smoothing kernel (e.g., using three voxels or another number of voxels) to determine derivatives for a set of amplitude scans (A-scans) within the B-scan.

Continuing with the example, positions of the outer-most boundaries in a given A-scan may be identified as the positions that have largest positive and negative derivative values, respectively. Additionally, the image processing platform may determine error values by comparing estimated positions of the outer-most boundaries with a median filtered surface. A voxel may be filtered if a position of the voxel is not within a threshold distance of the median filtered surface. A voxel may be filtered at a given position by being replaced with an interpolated voxel. In this case, the image processing platform may flatten the B-scan by vertically shifting each A-scan based on the estimated positions that have been filtered.

In some implementations, the image processing platform may normalize a B-scan that has been flattened. For example, the image processing platform may normalize the B-scan by identifying or determining a set of intensity values associated with voxels within the B-scan and by normalizing the set of intensity values.

In some implementations, the image processing platform may determine a set of spatial coordinates for a B-scan that has been flattened. For example, the image processing platform may determine a set of spatial coordinates in a manner that assigns an x-coordinate and a y-coordinate to each voxel of a set of voxels of the B-scan. In some implementations, the image processing platform may have a pre-configured array that represents the set of spatial coordinates and may map values of the array to voxels of the B-scan.

As shown by reference number 115, the image processing platform may obtain a data model from the data storage device. For example, one or more aspects of a data model may be available from a third-party data source, and the image processing platform may perform a search query to download the data model from the data storage device. The data model may be a neural network, such as a convolutional neural network (CNN), a fully convolutional neural network (FCN), a U-net, and/or a similar type of neural network.

In some implementations, the image processing platform may receive a U-net. The U-net may include an input layer, a set of intermediate layers (with no fully connected layer), and an output layer. The set of intermediate layers include a first intermediate layer that may be used to generate a set of boundary maps, a second intermediate layer that may be used to determine an initial set of boundary positions, and a third intermediate layer that may be used to determine final boundary positions for layers of a macula, where the final boundary positions have a correct topological ordering. In some implementations, one or more aspects of the U-net may be customized for automatic layer segmentation (e.g., before training the U-net, while training the U-net, etc.), as described below.

As shown by reference number 120, the image processing platform may train the data model. For example, if the data model is a neural network, such as the U-net, the image processing platform may train the U-net to be able to receive a B-scan as an input and to generate boundary maps that indicate likelihoods of voxels in the B-scan being in positions that are part of particular boundaries.

A boundary map may be an array of probability values that indicate likelihoods of voxels of the B-scan being in positions that are part of particular boundaries. Additionally, probability values within a boundary map may be generated such that probability values for voxels that share a y-coordinate may add up to one. This is because the image processing platform may generate probability values for each corresponding column of voxels within a B-scan (e.g., where a column of voxels includes voxels that share a y-coordinate). Additionally, a number of boundary maps that are generated for a given B-scan may correspond to a number of boundaries (e.g., if there are nine boundaries, the image processing platform may generate nine boundary maps).

In some implementations, the image processing platform may customize one or more aspects of the U-net. For example, the image processing platform may customize a cost function of the U-net. The cost function may include a smooth L1 loss function, a means squared error (MSE) function, and/or another type of L1 or L2 function. In this case, the image processing platform may train the U-net to approximate a conditional distribution of training data (e.g., B-scans, etc.). The conditional distribution may be a boundary probability map given an input B-scan. The probability map may represent a probability that actual boundary positions are at a given position. To determine loss, the image processing platform may apply a Kullback-Leibler (K-L) divergence technique to measure similarity between a given input distribution and a ground truth distribution. By minimizing a K-L divergence value (i.e., a loss value), the U-net is effectively trained to output distributions that are similar to the ground truth distribution.

Additionally, or alternatively, the image processing platform may customize the U-net by configuring the U-net with a fully differentiable soft argmax function. For example, the U-net may output a conditional distribution for each column, which allows an exact inference of a boundary position at a given column to be able to be calculated independently. As such, the image processing platform may configure the U-net with a fully differentiable soft argmax function that is able to estimate a final boundary position at each column i. The soft argmax function may be fully differentiable with respect to each input value processed by the function. An example of the soft argmax function may be found in the appendix (see, e.g., Page 4, Equation 5).

In some implementations, the image processing platform may receive a trained data model. For example, the data model may be trained by a device of a software developer and provided to the image processing platform after being trained.

In this way, the image processing platform is able to configure the data model with a cost function that will account for a degree to which probability values represent actual boundary positions.

Figure 1C:
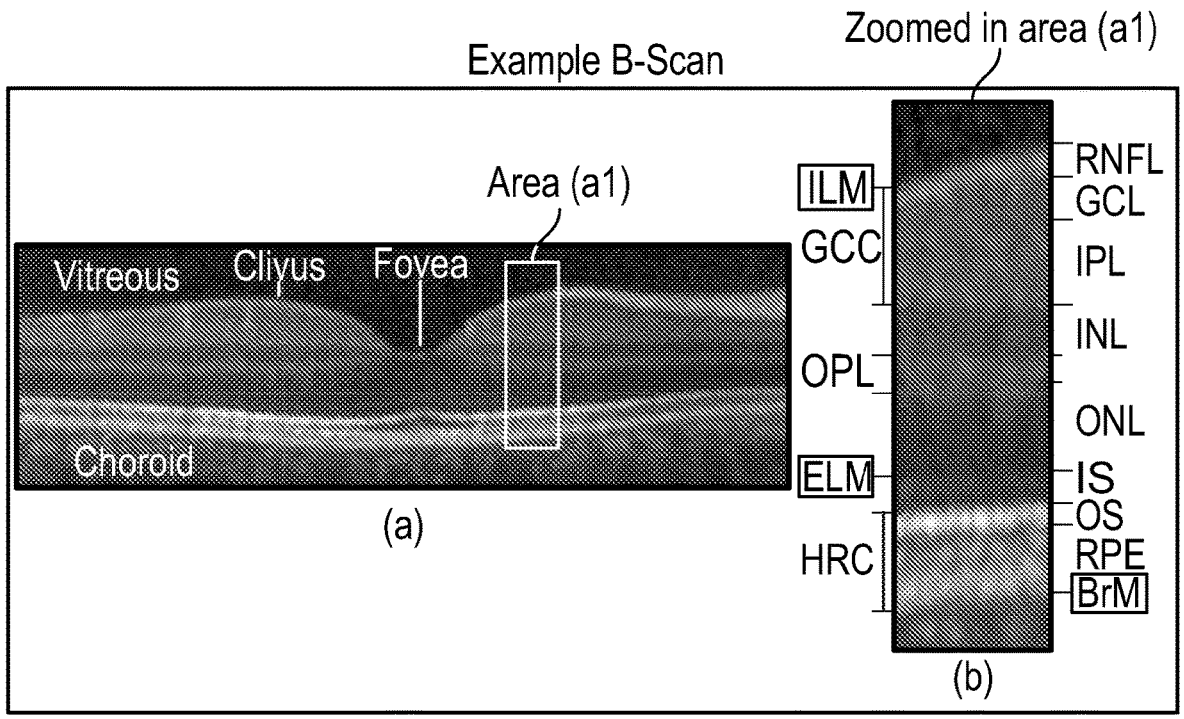
Figure 1C:
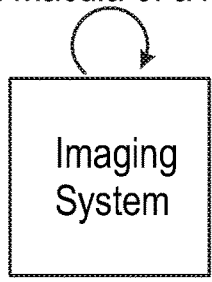
Figure 1C:
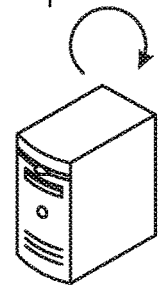

As shown in FIG. 1C, and by reference number 125, the imaging system may generate a set of B-scans that depict a macula of an eye of a patient that is being tested for an eye disorder or a neurological disorder. For example, the imaging system may be positioned in a manner that allows a lens of an image capturing component to be zoomed in on the eye of the patient. In this case, the imaging system may take a series of images of the eye to generate the set of B-scans.

As shown by reference number 130, the imaging system may provide the set of B-scans to the image processing platform. For example, the imaging system may provide the set of B-scans to the image processing platform using a communication interface, such as an application programming interface (API) or a similar type of interface. In some implementations, the imaging system may provide the set of B-scans to one or more intermediary devices which may provide the set of B-scans to the image processing platform.

As shown by reference number 135, the image processing platform may perform one or more pre-processing operations. For example, the image processing platform may perform one or more pre-processing operations to convert the set of B-scans to a standardized format, and to determine or identify a set of spatial coordinates of voxels within the set of B-scans, as described elsewhere herein.

In this way, the image processing platform is able to receive a set of B-scans and to perform one or more pre-processing operations that will allow the set of B-scans to be further processed by the data model.

Figure 1D:
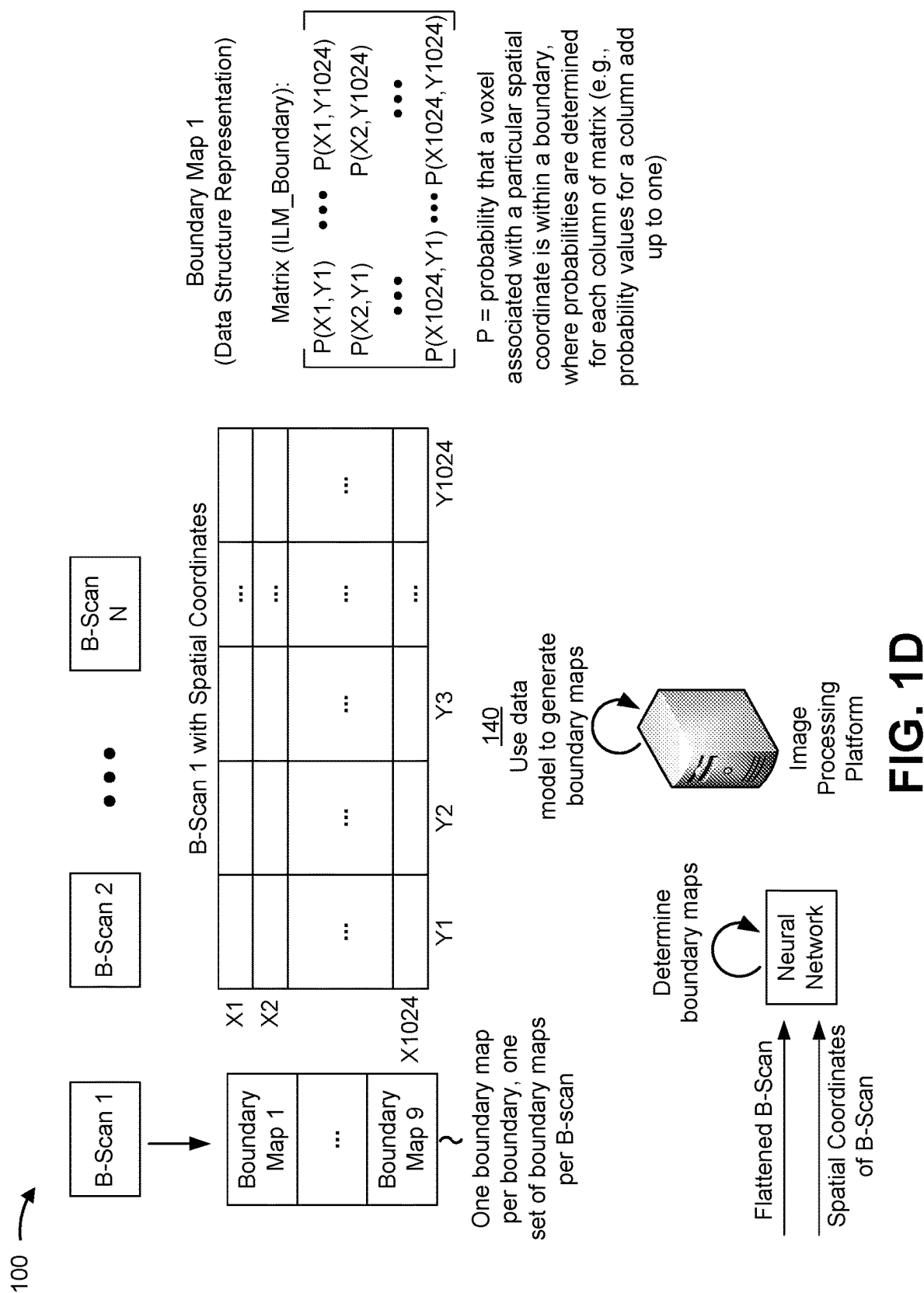

As shown in FIG. 1D, and by reference number 140, the image processing platform may use the data model (e.g., the U-net) to generate a set of boundary maps. For example, the image processing platform may provide the set of B-scans that have been pre-processed (e.g., flattened) and data that identifies the set of spatial coordinates as input to the U-net. This may cause the U-net to generate a set of boundary maps that indicate likelihoods of voxels within the set of B-scans being in positions that are part of particular boundaries. A probability value given to a voxel (which represents a particular likelihood) may be relative to other voxels that share a y-coordinate with the voxel (as further explained in the example below). In this case, the image processing platform may, for a given B-scan, generate a boundary map for each boundary of the boundaries used to segment the set of layers of the macula. The image processing platform may generate these boundary maps for each B-scan of the set of B-scans.

In the example shown, the image processing platform may, for a particular B-scan, generate a boundary map for the ILM boundary. In this example, the boundary map may be an array of values that identifies, for each voxel in the particular B-scan, a likelihood of each voxel being within the ILM boundary. Additionally, each column of voxels in a B-scan (e.g., that share a y-coordinate value) may include probability values that collectively add up to a value of one. For example, for a first column in a B-scan (shown as Y-coordinate Y1), if there are 1024 rows of voxels, then the boundary map for the first column may be an array of 1024 values that add up to the value of one. By generating probability values per column, the image processing platform ensures that an appropriate layer topology will be preserved when a final set of boundary positions are determined, as described further herein.

In this way, the image processing platform is able to use the data model to generate the set of boundary maps.

Figure 1E:
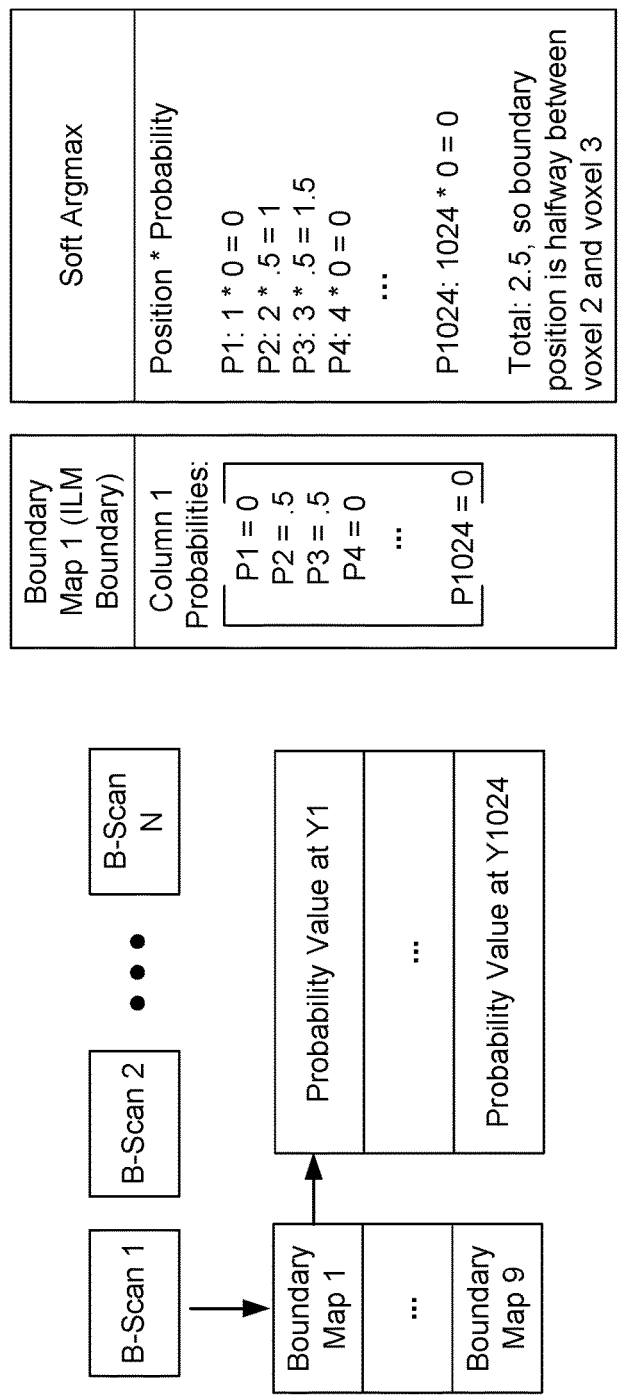
Figure 1E:
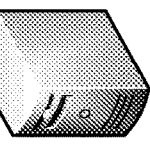

As shown in FIG. 1E, and by reference number 145, the image processing platform may determine an initial set of boundary positions by using a soft argmax function of the data model to analyze the set of boundary maps. For example, the set of boundary maps may be provided as input to another intermediate layer within the U-net, and the image processing platform may execute a soft argmax function to determine the initial set of boundary positions. As shown, the image processing platform may determine initial boundary positions for each boundary map for each B-scan. Additionally, the image processing platform may, for a boundary map of a B-scan, determine one initial boundary position per y-coordinate in the set of spatial coordinates of the B-scan.

As shown as an example, the image processing platform may execute the soft argmax function to determine, for the ILM boundary, an initial boundary position for a first column of a B-scan. In this example, the image processing platform may use the soft argmax function to multiply each spatial coordinate value in the first column against a probability value of a corresponding boundary map. Specifically, the image processing platform may multiply a value one by a value of zero (for a first position in the first column), may multiply a value of two by a value of 0.5 (for a second position in the first column), may multiply a value of three by a value of 0.5 (for a third position in the first column), and may repeat this for each position (i.e., each spatial coordinate) within the first column. Next, the image processing platform may determine a total by adding a result of each respective multiplication operation. In this example, the total is a value of 2.5, which represents that for the first column, the ILM boundary is predicted to be located halfway between a second voxel and a third voxel.

In this way, the image processing platform determines an initial set of boundary positions.

Figure 1F:
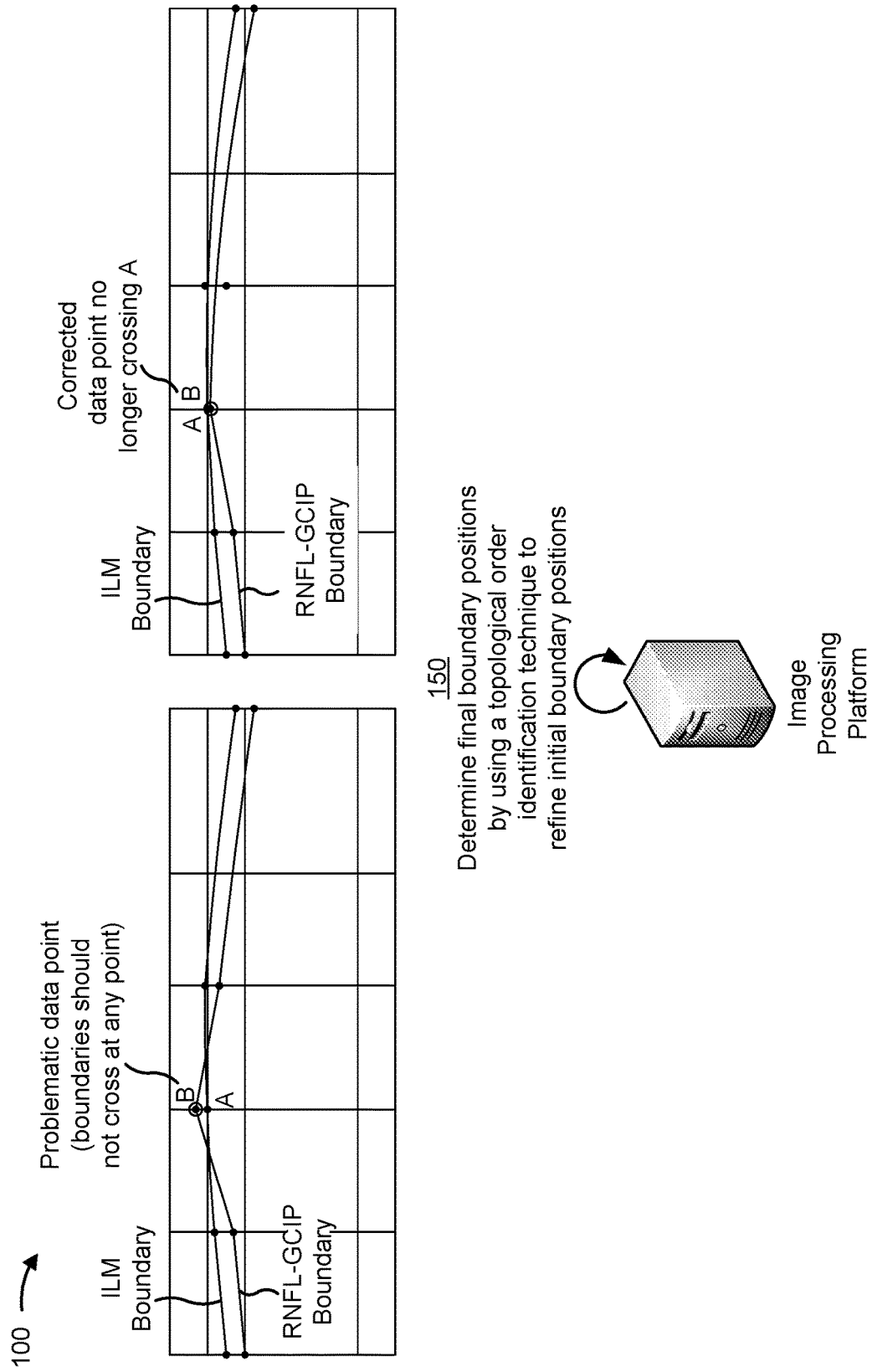

As shown in FIG. 1F, and by reference number 150, the image processing platform may determine a final set of boundary positions by using a topological order identification technique to refine the initial set of boundary positions. For example, the image processing platform may provide the initial set of boundary positions to a final intermediate layer of the U-net that is able to analyze the initial set of boundaries using a topological order identification technique. The topological order identification technique may, based on the analysis, determine the final set of boundary positions in a manner that prevents the boundaries from overlapping with each other. The topological order identification technique may include a set of rules that allow the U-net to verify and/or modify each boundary position of the initial set of boundary positions. An example of implementing the set of rules is provided below.

As shown as an example, the image processing platform may identify a first data point (shown as data point A) that is associated with the ILM boundary and may identify a second data point (shown as data point B) that is associated with the RNFL-GCIP boundary. In this example, the image processing platform may identify the second data point as a problematic data point based on the second data point having a position that overlaps with a corresponding position (data point A) of the ILM boundary. Because the second data point cannot be reconciled with an appropriate layer topology (layers in the macula do not overlap), the image processing platform may apply the topological order identification technique in a manner that allows the second data point to be repositioned below the first data point.

In this way, the image processing platform determines the final set of boundary positions with sub-voxel precision and in a manner that preserves the appropriate layer topology.

Figure 1G:
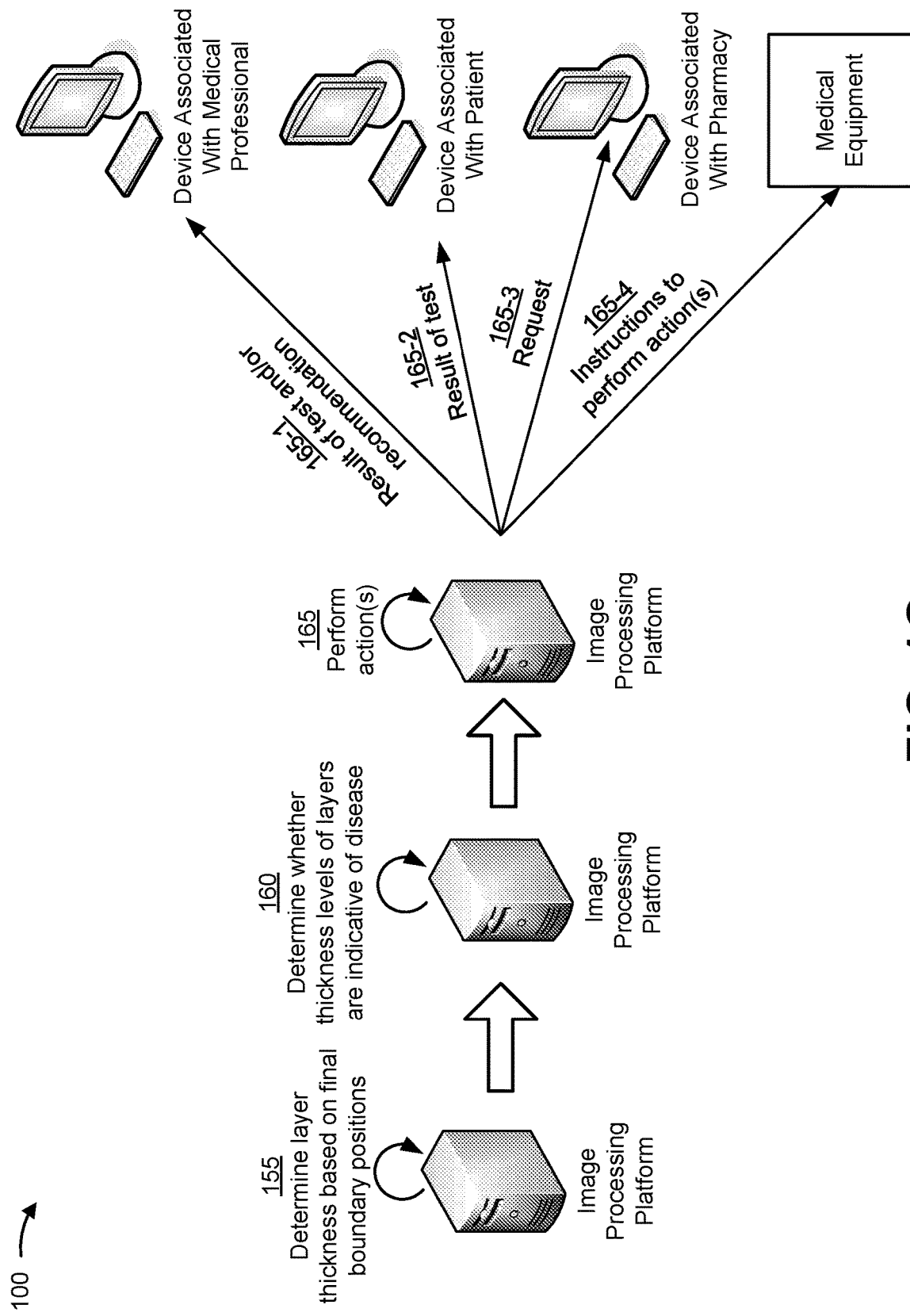

As shown in FIG. 1G, and by reference number 155, the image processing platform may determine a thickness of layers of the macula based on the final set of boundary positions. For example, the image processing platform may measure a distance between neighboring boundaries to determine a thickness of each layer of the macula.

As shown by reference number 160, the image processing platform may determine whether the thickness of one or more layers is indicative of a disease or neurological disorder. For example, the image processing platform may be configured with a set of measured thicknesses of particular layers of a macula as would be found in both healthy patients and patients who have a disease or a neurological disorder. In this case, the image processing platform may compare the set of measured thicknesses to the thickness of the set of layers of the macula that is being analyzed to determine whether one or more of the set of layers has a thickness that may be indicative of disease or neurological disorder.

As shown by reference number 165, the image processing platform may perform one or more actions. For example, the image processing platform may, based on determining whether the thickness of the one or more layers is indicative of a disease or neurological disorder, perform a first set of one or more actions to cause test results to be displayed on an interface of a device associated with a medical professional, perform a second set of one or more actions to cause a device associated with the patient to be provided with the test results, perform a third set of one or more actions to cause a prescription to be ordered for the patient, perform a fourth set of one or more actions to cause medical equipment to perform a procedure on the patient, and/or the like, as each described below.

As shown by reference number 165-1, the image processing platform may provide, to a device associated with a medical professional, test results data. For example, the image processing platform may generate the test results data based on determining whether the thickness of one or more layers of the patient's macula is indicative of a disease or order. In this case, the image processing platform may provide the test results data to the device associated with the medical professional (e.g., via text message, via electronic mail (e-mail), via an API, etc.). This may allow the medical professional to review the test results data and to make a medical recommendation for the patient.

As shown by reference number 165-2, the image processing platform may provide the test results data to a device (or account) associated with a patient. For example, the image processing platform may provide the test results data to the device (or account) associated with the patient via text message, via e-mail, via an API, and/or via another type of communication interface. This may notify the patient of the test results and, in some cases, may instruct the patient on a next step (e.g., to begin a treatment plan, etc.).

As shown by reference number 165-3, the image processing platform may provide, to a device associated with a pharmacy, a request for a prescription medication that may be used to treat or cure a disease or disorder. For example, the image processing platform may generate the request by populating a form with patient data and may use a communication interface described above to provide the request to the device associated with the pharmacy. In, this case, the request may also be provided to the device associated with the medical professional (e.g., to allow the medical professional to sign off on the prescription medication).

As shown by reference number 165-4, the image processing platform may provide, to particular medical equipment, a set of instructions to perform one or more actions. For example, if the patient is found to have a disease or disorder, there may be immediate treatment available. In this case, the image processing platform may generate a set of instructions for a machine that is able to perform one or more aspects of the treatment to permit the machine to perform the treatment. As an example, a robotic arm may be tasked with performing a procedure on the patient's eye, and the image processing platform may instruct the robotic arm to perform the procedure.

In some implementations, the image processing platform may perform one or more additional actions. For example, the image processing platform may receive feedback information from a user device and may retrain the data model based on the feedback information.

While one or more implementations described herein involve determining whether a patient has a disease or disorder, it is to be understood that this is provided by way of example. In practice, one or more implementations described herein may be used for other purposes, such as for determining thickness of layers of the macula to determine whether the patient's treatment has been working effectively (e.g., by slowing a gradual thinning of particular layers of the macula), determining a degree to which a disease or disease has advanced or accelerated over time, and/or the like.

In this way, the image processing platform is able to identify the boundaries that segment the layers of the macula. Furthermore, by identifying the boundaries with voxel or sub-voxel precision and in a manner that preserves the topology of the layers, the image processing platform efficiently and effectively utilizes resources (e.g., processing resources, network resources, and/or the like) relative to one or more inferior automatic segmentation techniques.

As indicated above, FIGS. 1A-1G are provided merely as one or more examples. Other examples may differ from what is described with regard to FIGS. 1A-1G. For example, there may be additional devices and/or networks, fewer devices and/or networks, different devices and/or networks, or differently arranged devices and/or networks than those shown in FIGS. 1A-1G. Furthermore, two or more devices shown in FIGS. 1A-1G may be implemented within a single device, or a single device shown in FIGS. 1A-1G may be implemented as multiple and/or distributed devices. Additionally, or alternatively, a set of devices (e.g., one or more devices) included in the one or more example implementations 100 may perform one or more functions described as being performed by another set of devices included in the one or more example implementations 100.

Figure 2:
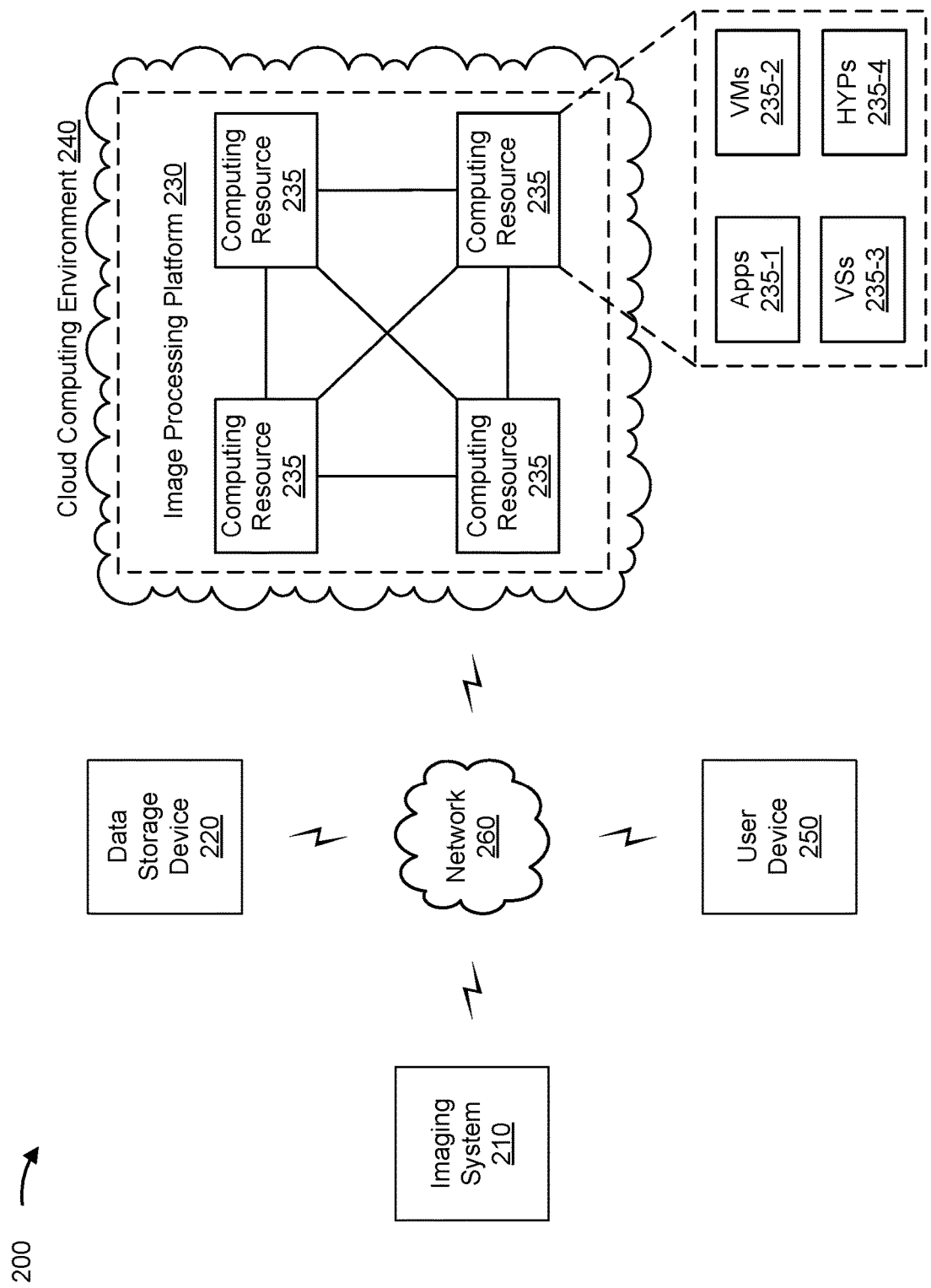
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include an imaging system 210, a data storage device 220, an image processing platform 230 in a cloud computing environment 240 that includes a set of computing devices 235, a user device 250, and a network 260. Devices of environment 200 may interconnect via wired connections, wireless connections, or a combination of wired and wireless connections.

Imaging system 210 includes one or more devices capable of receiving, storing, generating, determining, and/or providing information associated with a set of images (e.g., a set of B-scans). For example, imaging system 210 may include a magnetic resonance imaging (MRI) device, an X-ray computed tomography (CT) scan device, a positron emission tomography (PET) device, an ultrasound imaging (USI) device, a photoacoustic imaging (PAI) device, a device capable of performing optical coherence tomography (OCT), and/or a similar type of device. In some implementations, imaging system 210 may generate and provide image processing platform 230 with a set of B-scans.

Data storage device 220 includes one or more devices capable of receiving, storing, generating, determining, and/or providing information associated with training data (e.g., a labeled set of B-scans) and/or a data model. For example, data storage device 220 may include a server device or a group of server devices. In some implementations, a first data storage device 220 may store training data that may be used to train a data model, as described elsewhere herein. In some implementations, a second data storage device 220 may store a trained neural network, such as a U-net (i.e., a specific type of fully convolutional neural network (FCN)).

Image processing platform 230 includes one or more devices capable of receiving, storing, generating, determining, and/or providing information associated with an optical coherence tomography (OCT) volume. For example, image processing platform 230 may include a server device (e.g., a host server, a web server, an application server, etc.), a data center device, or a similar device. In some implementations, image processing platform 230 may receive training data from data storage device 220. In some implementations, image processing platform 230 may receive a set of B-scans from imaging system 210. In some implementations, image processing platform 230 may determine a final set of boundary positions for layers of a macula and may use the final set of boundary positions to determine a thickness of the layers, as described elsewhere herein. In some implementations, image processing platform 230 may interact with user device 250 to perform one or more actions described herein.

In some implementations, as shown, image processing platform 230 may be hosted in cloud computing environment 240. While implementations described herein describe image processing platform 230 as being hosted in cloud computing environment 240, in some implementations, image processing platform 230 might not be cloud-based (i.e., may be implemented outside of a cloud computing environment) or may be partially cloud-based.

Cloud computing environment 240 includes an environment that hosts image processing platform 230. Cloud computing environment 240 may provide computation, software, data access, storage, etc. services that do not require end-user knowledge of a physical location and configuration of system(s) and/or device(s) that hosts image processing platform 230. As shown, cloud computing environment 240 may include a group of computing resources 235 (referred to collectively as "computing resources 235" and individually as "computing resource 235").

Computing resource 235 includes one or more personal computers, workstation computers, server devices, or another type of computation and/or communication device. In some implementations, computing resource 235 may host image processing platform 230. The cloud resources may include compute instances executing in computing resource 235, storage devices provided in computing resource 235, data transfer devices provided by computing resource 235, and/or the like. In some implementations, computing resource 235 may communicate with other computing resources 235 via wired connections, wireless connections, or a combination of wired and wireless connections.

As further shown in FIG. 2, computing resource 235 may include a group of cloud resources, such as one or more applications ("APPs") 235-1, one or more virtual machines ("VMs") 235-2, virtualized storage ("VSs") 235-3, one or more hypervisors ("HYPs") 235-4, and/or the like.

Application 235-1 may include one or more software applications that may be provided to or accessed by imaging system 210, data storage device 220, and/or user device 250. Application 235-1 may eliminate a need to install and execute the software applications on these devices. For example, application 235-1 may include software associated with image processing platform 230 and/or any other software capable of being provided via cloud computing environment 240. In some implementations, one application 235-1 may send/receive information to/from one or more other applications 235-1, via virtual machine 235-2.

Virtual machine 235-2 may include a software implementation of a machine (e.g., a computer) that executes programs like a physical machine. Virtual machine 235-2 may be either a system virtual machine or a process virtual machine, depending upon use and degree of correspondence to any real machine by virtual machine 235-2. A system virtual machine may provide a complete system platform that supports execution of a complete operating system ("OS"). A process virtual machine may execute a single program and may support a single process. In some implementations, virtual machine 235-2 may execute on behalf of another device (e.g., imaging system 210, data storage device 220, and/or user device 250, etc.), and may manage infrastructure of cloud computing environment 240, such as data management, synchronization, or long-duration data transfers.

Virtualized storage 235-3 may include one or more storage systems and/or one or more devices that use virtualization techniques within the storage systems or devices of computing resource 235. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 235-4 may provide hardware virtualization techniques that allow multiple operating systems (e.g., "guest operating systems") to execute concurrently on a host computer, such as computing resource 235. Hypervisor 235-4 may present a virtual operating platform to the guest operating systems and may manage the execution of the guest operating systems. Multiple instances of a variety of operating systems may share virtualized hardware resources.

User device 250 includes one or more devices capable of receiving, generating, storing, processing, and/or providing information associated with a test result. For example, user device 250 may include a device or machine, such as a mobile phone (e.g., a smart phone, a radiotelephone, etc.), medical equipment, a laptop computer, a tablet computer, a handheld computer, a server computer, a gaming device, a wearable communication device (e.g., a smart wristwatch, a pair of smart eyeglasses, etc.), or a similar type of device or machine.

In some implementations, user device 250 may be a device of a doctor and may receive, from image processing platform 230, data that identifies a test result and/or a recommendation associated with the test result. In some implementations, user device 250 may be a device associated with a patient and may receive data that identifies the test result from image processing platform 230. In some implementations, user device 250 may be a device associated with a pharmacy and may receive, from image processing platform 230, a request for medication that may assist with one or more symptoms of a disease, with curing the disease, and/or the like. In some implementations, user device 250 may receive, from image processing platform 230, a set of instructions to perform one or more actions described elsewhere herein.

Network 260 includes one or more wired and/or wireless networks. For example, network 260 may include a cellular network (e.g., a fifth generation (5G) network, a fourth generation (4G) network, such as a long-term evolution (LTE) network, a third generation (3G) network, a code division multiple access (CDMA) network, a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 2 are provided as one or more examples. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
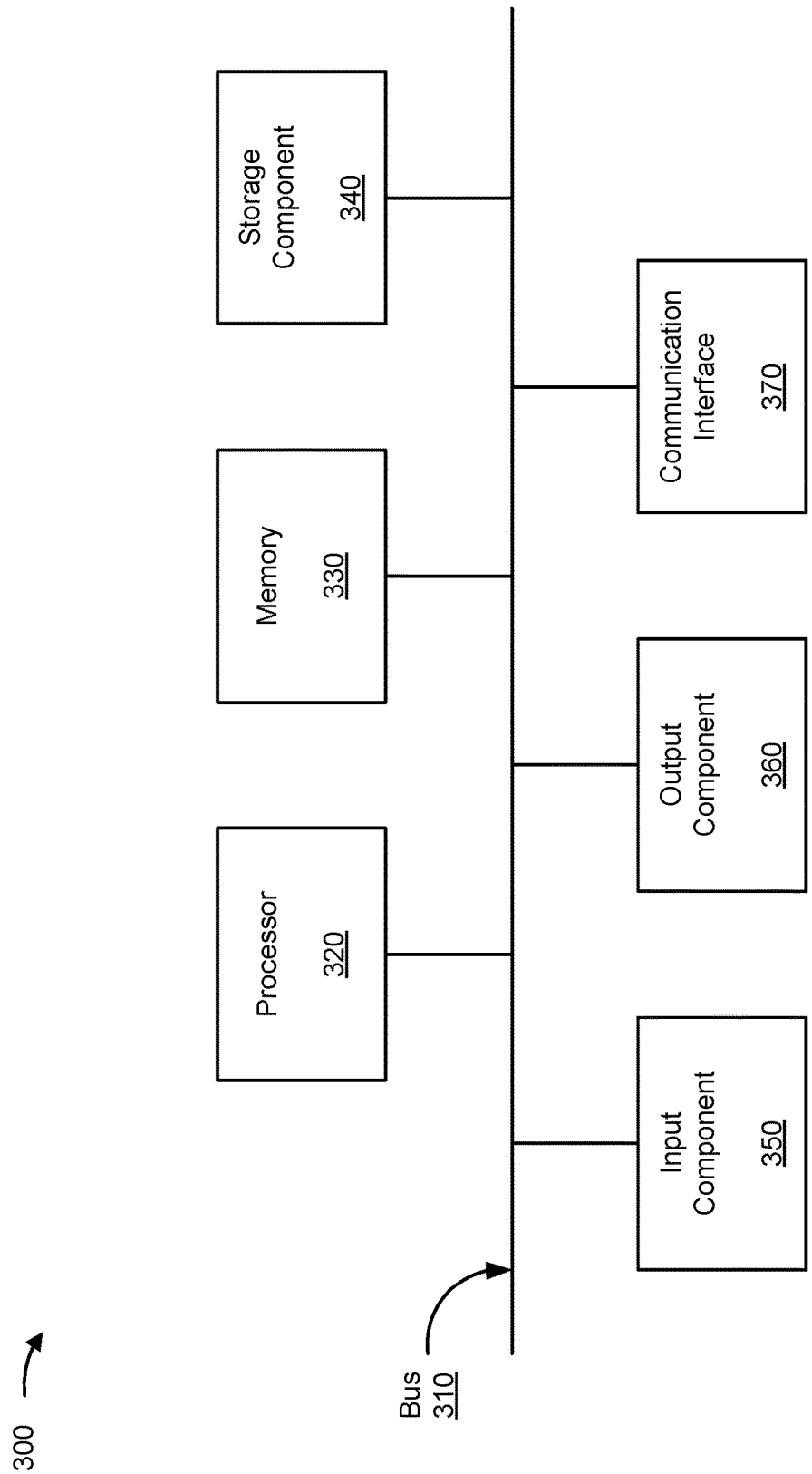
FIG. 3 is a diagram of example components of one or more devices of FIG. 2.

FIG. 3 is a diagram of example components of a device 300. Device 300 may correspond to imaging system 210, data storage device 220, image processing platform 230, computing resource 235, and/or user device 250. In some implementations, imaging system 210, data storage device 220, image processing platform 230, computing resource 235, and/or user device 250 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among multiple components of device 300. Processor 320 is implemented in hardware, firmware, and/or a combination of hardware and software. Processor 320 includes a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), and/or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, and/or a magneto-optic disk), a solid state drive (SSD), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a component for determining location (e.g., a global positioning system (GPS) component) and/or a sensor (e.g., an accelerometer, a gyroscope, an actuator, another type of positional or environmental sensor, and/or the like). Output component 360 includes a component that provides output information from device 300 (via, e.g., a display, a speaker, a haptic feedback component, an audio or visual indicator, and/or the like).

Communication interface 370 includes a transceiver-like component (e.g., a transceiver, a separate receiver, a separate transmitter, and/or the like) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. As used herein, the term "computer-readable medium" refers to a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
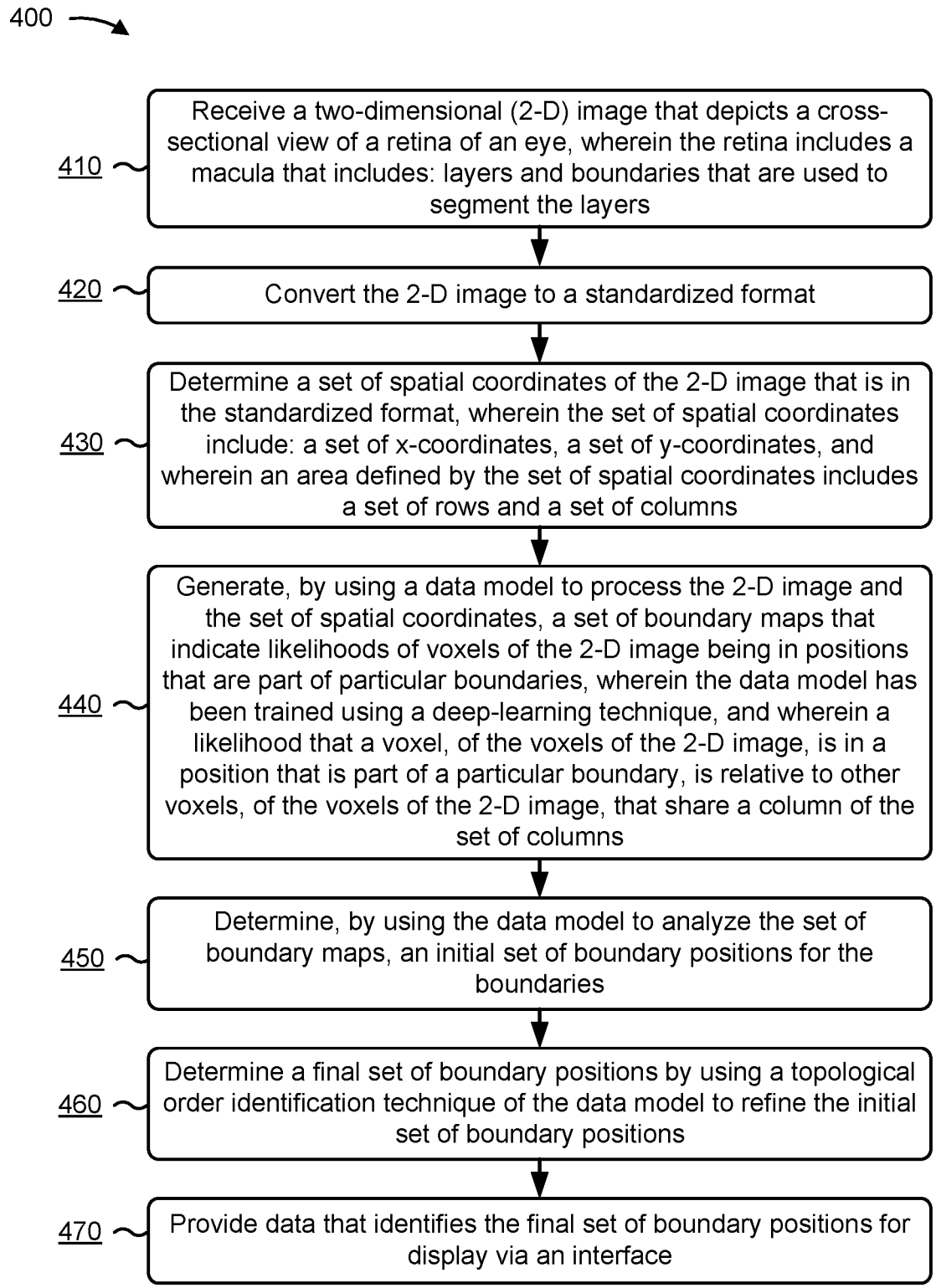
FIGS. 4-6 are flowcharts of example processes for determining boundary positions of boundaries that are used to segment layers of a macula by using a neural network to analyze a set of images that depict a cross-sectional view of the macula.

FIG. 4 is a flow chart of an example process 400 for determining boundary positions of boundaries that are used to segment layers of a macula by using a neural network to analyze a set of images that depict a cross-sectional view of the macula. In some implementations, one or more process blocks of FIG. 4 may be performed by an image processing platform (e.g., image processing platform 230). In some implementations, one or more process blocks of FIG. 4 may be performed by another device or a group of devices separate from or including the image processing platform, such as an imaging system (e.g., imaging system 210), a data storage device (e.g., data storage device 220), a user device (e.g., user device 250), and/or the like.

As shown in FIG. 4, process 400 may include receiving a two-dimensional (2-D) image that depicts a cross-sectional view of a retina of an eye, wherein the retina includes a macula that includes: layers, and boundaries that are used to segment the layers (block 410). For example, the image processing platform (e.g., using computing resource 235, processor 320, memory 330, storage component 340, input component 350, communication interface 370, and/or the like) may receive a two-dimensional (2-D) image that depicts a cross-sectional view of a retina of an eye, as described above. In some implementations, the retina may include a macula that includes: layers, and boundaries that are used to segment the layers.

As further shown in FIG. 4, process 400 may include converting the 2-D image to a standardized format (block 420). For example, the image processing platform (e.g., using computing resource 235, processor 320, memory 330, storage component 340, and/or the like) may convert the 2-D image to a standardized format, as described above.

As further shown in FIG. 4, process 400 may include determining a set of spatial coordinates of the 2-D image that is in the standardized format, wherein the set of spatial coordinates include: a set of x-coordinates, a set of y-coordinates, and wherein an area defined by the set of spatial coordinates includes a set of rows and a set of columns (block 430). For example, the image processing platform (e.g., using computing resource 235, processor 320, memory 330, storage component 340, and/or the like) may determine a set of spatial coordinates of the 2-D image that is in the standardized format, as described above. In some implementations, the set of spatial coordinates may include a set of x-coordinates, and a set of y-coordinates. In some implementations, an area defined by the set of spatial coordinates includes a set of rows and a set of columns As further shown in FIG. 4, process 400 may include generating, by using a data model to process the 2-D image and the set of spatial coordinates, a set of boundary maps that indicate likelihoods of voxels of the 2-D image being in positions that are part of particular boundaries, wherein the data model has been trained using a deep-learning technique, and wherein a likelihood that a voxel, of the voxels of the 2-D image, is in a position that is part of a particular boundary, is relative to other voxels, of the voxels of the 2-D image, that share a y-coordinate of the set of y-coordinates with the voxel of the voxels (block 440). For example, the image processing platform (e.g., using computing resource 235, processor 320, memory 330, storage component 340, and/or the like) may generate, by using a data model to process the 2-D image and the set of spatial coordinates, a set of boundary maps that indicate likelihoods of voxels of the 2-D image being in positions that part of particular boundaries, as described above. In some implementations, the data model has been trained using a deep-learning technique. In some implementations, a likelihood that a voxel, of the voxels of the 2-D image, is in a position that is part of a particular boundary, may be relative to other voxels, of the voxels of the 2-D image, that share a y-coordinate of the set of y-coordinates with the voxel of the voxels.

As further shown in FIG. 4, process 400 may include determining, by the device and by using the data model to analyze the set of boundary maps, an initial set of boundary positions for the boundaries (block 450). For example, the image processing platform (e.g., using computing resource 235, processor 320, memory 330, storage component 340, and/or the like) may determine, by the device and by using the data model to analyze the set of boundary maps, an initial set of boundary positions for the boundaries, as described above.

As further shown in FIG. 4, process 400 may include determining a final set of boundary positions by using a topological order identification technique of the data model to refine the initial set of boundary positions (block 460). For example, the image processing platform (e.g., using computing resource 235, processor 320, memory 330, storage component 340, and/or the like) may determine a final set of boundary positions by using a topological order identification technique of the data model to refine the initial set of boundary positions, as described above.

As further shown in FIG. 4, process 400 may include providing data that identifies the final set of boundary positions for display via an interface (block 470). For example, the image processing platform (e.g., using computing resource 235, processor 320, memory 330, storage component 340, output component 360, communication interface 370, and/or the like) may provide data that identifies the final set of boundary positions for display via an interface, as described above.

Process 400 may include additional implementations, such as any single implementation or any combination of implementations described below and/or in connection with one or more other processes described elsewhere herein.

In some implementations, the data model may be trained using a cost function that accounts for a degree to which a probability value matches a ground truth value that represents an actual boundary position of a boundary of the boundaries. In some implementations, when determining the initial set of boundary positions, the image processing platform may use a soft argmax function of the data model to analyze a boundary map of the set of boundary maps, where the initial set of boundary positions include a boundary position for each y-coordinate of the set of y-coordinates, and wherein the soft argmax function is fully differentiable with respect to each variable input to the soft argmax function.

In some implementations, when determining the final set of boundary positions, the image processing platform may use the topological order identification technique to determine the final set of boundary positions in a manner to prevent the boundaries from overlapping with each other. In some implementations, the data model may be a convolutional neural network (CNN) and the topological order identification technique utilizes one or more rectifiers and is a final output layer of the CNN.

In some implementations, when determining the final set of boundary positions, the image processing platform may identify a first position of a first voxel, of the voxels of the 2-D image, that is associated with a first boundary, and may identify a second position of a second voxel, of the voxels of the 2-D image, that is associated with a second boundary that is in an expected position relative to the first boundary, where the first voxel and the second voxel share a particular y-coordinate of the set of y-coordinates, Additionally, the image processing platform may determine, by comparing the first position and the second position, that the second position is not in the expected position relative to the first position, and may modify the first position or the second position in a manner that allows the first position to be positioned in the expected position.

In some implementations, the image processing platform may determine, after determining the final set of boundary positions, thickness levels of the layers of the macula based on the final set of boundary positions, and may determine whether the thickness levels of the layers are indicative of a disease, wherein providing the data that identifies the final set of boundary positions for display via the interface comprises providing, for display via the interface, an indication of whether the thickness levels of the layers are indicative of the disease.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
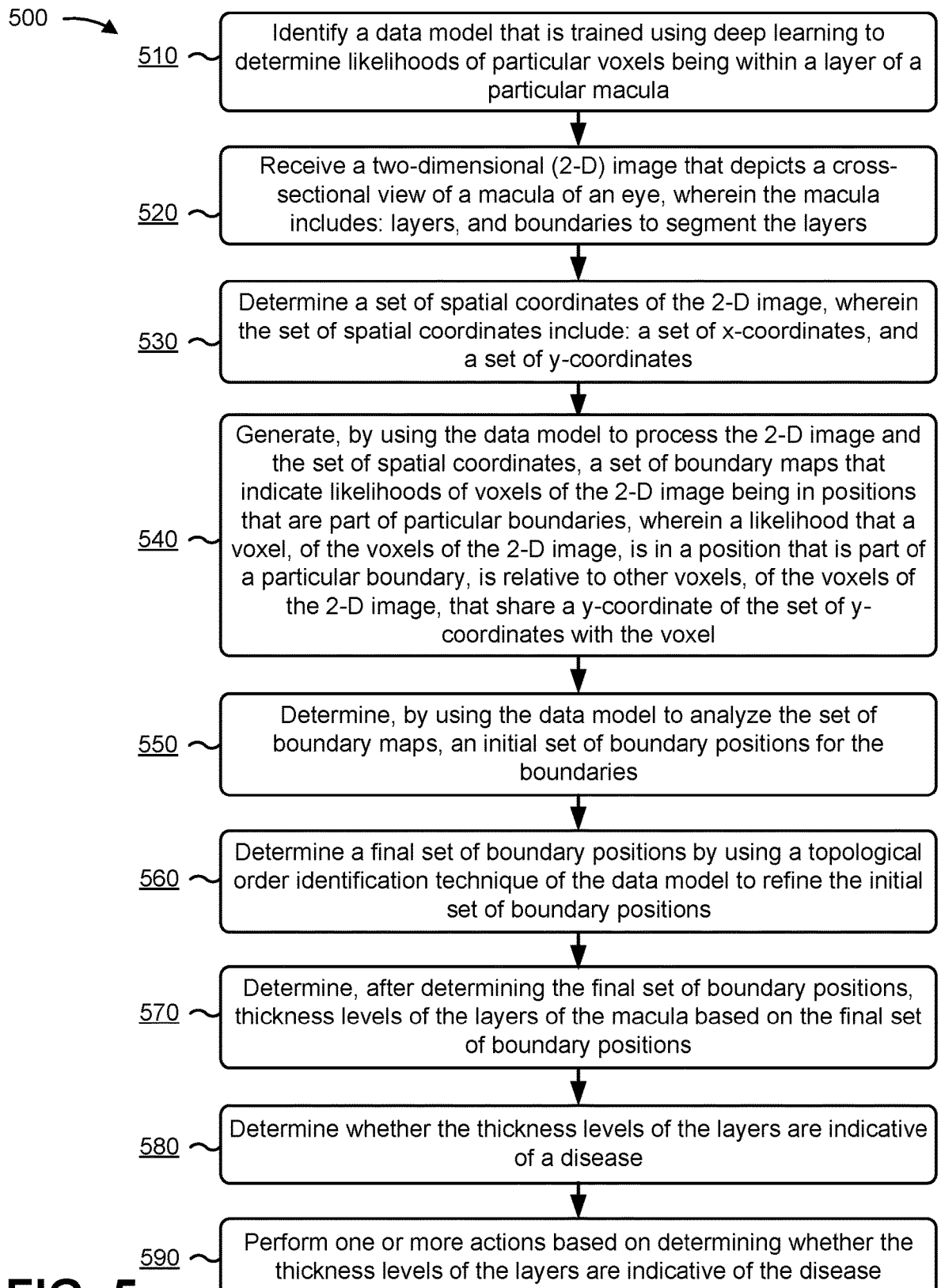

FIG. 5 is a flow chart of an example process 500 for determining boundary positions of boundaries that are used to segment layers of a macula by using a neural network to analyze a set of images that depict a cross-sectional view of the macula. In some implementations, one or more process blocks of FIG. 6 may be performed by an image processing platform (e.g., image processing platform 230). In some implementations, one or more process blocks of FIG. 5 may be performed by another device or a group of devices separate from or including the image processing platform, such as an imaging system (e.g., imaging system 210), a data storage device (e.g., data storage device 220), a user device (e.g., user device 250), and/or the like.

As shown in FIG. 5, process 500 may include identifying a data model that is trained using deep learning to determine likelihoods of particular voxels being within a layer of a particular macula (block 510). For example, the image processing platform (e.g., using computing resource 235, processor 320, memory 330, storage component 340, and/or the like) may identify a data model that is trained using deep learning to determine likelihoods of particular voxels being within a layer of a particular macula, as described above.

As further shown in FIG. 5, process 500 may include receiving a two-dimensional (2-D) image that depicts a cross-sectional view of a macula of an eye, wherein the macula includes: layers, and boundaries to segment the layers (block 520). For example, the image processing platform (e.g., using computing resource 235, processor 320, memory 330, storage component 340, input component 350, communication interface 370, and/or the like) may receive a two-dimensional (2-D) image that depicts a cross-sectional view of a macula of an eye, as described above. In some implementations, the macula may include layers, and boundaries to segment the layers.

As further shown in FIG. 5, process 500 may include determining a set of spatial coordinates of the 2-D image, wherein the set of spatial coordinates include: a set of x-coordinates, and a set of y-coordinates (block 530). For example, the image processing platform (e.g., using computing resource 235, processor 320, memory 330, storage component 340, and/or the like) may determine a set of spatial coordinates of the 2-D image, as described above. In some implementations, the set of spatial coordinates may include a set of x-coordinates, and a set of y-coordinates, As further shown in FIG. 5, process 500 may include generating, by using the data model to process the 2-D image and the set of spatial coordinates, a set of boundary maps that indicate likelihoods of voxels of the 2-D image being in positions that are part of particular boundaries, wherein a likelihood that a voxel, of the voxels of the 2-D image, is in a position that is part of a particular boundary is relative to other voxels, of the voxels of the 2-D image, that share a y-coordinate of the set of y-coordinates with the voxel (block 540). For example, the image processing platform (e.g., using computing resource 235, processor 320, memory 330, storage component 340, and/or the like) may generate, by using the data model to process the 2-D image and the set of spatial coordinates, a set of boundary maps that indicate likelihoods of voxels of the 2-D image being in positions that are part of particular boundaries, as described above. In some implementations, a likelihood that a voxel, of the voxels of the 2-D image, is in a position that is part of a particular boundary may be relative to other voxels, of the voxels of the 2-D image, that share a y-coordinate of the set of y-coordinates with the voxel.

As further shown in FIG. 5, process 500 may include determining, by using the data model to analyze the set of boundary maps, an initial set of boundary positions for the boundaries (block 550). For example, the image processing platform (e.g., using computing resource 235, processor 320, memory 330, storage component 340, and/or the like) may determine, by using the data model to analyze the set of boundary maps, an initial set of boundary positions for the boundaries, as described above.

As further shown in FIG. 5, process 500 may include determining a final set of boundary positions by using a topological order identification technique of the data model to refine the initial set of boundary positions (block 560). For example, the image processing platform (e.g., using computing resource 235, processor 320, memory 330, storage component 340, and/or the like) may determine a final set of boundary positions by using a topological order identification technique of the data model to refine the initial set of boundary positions, as described above.

As further shown in FIG. 5, process 500 may include determining, after determining the final set of boundary positions, thickness levels of the layers of the macula based on the final set of boundary positions (block 570). For example, the image processing platform (e.g., using computing resource 235, processor 320, memory 330, storage component 340, and/or the like) may determine, after determining the final set of boundary positions, thickness levels of the layers of the macula based on the final set of boundary positions, as described above.

As further shown in FIG. 5, process 500 may include determining whether the thickness levels of the layers are indicative of a disease (block 580). For example, the image processing platform (e.g., using computing resource 235, processor 320, memory 330, storage component 340, and/or the like) may determine whether the thickness levels of the layers are indicative of a disease, as described above.

As further shown in FIG. 5, process 500 may include performing one or more actions based on determining whether the thickness levels of the layers are indicative of the disease (block 590). For example, the image processing platform (e.g., using computing resource 235, processor 320, memory 330, storage component 340, input component 350, output component 360, communication interface 370, and/or the like) may perform one or more actions based on determining whether the thickness levels of the layers are indicative of the disease, as described above.

Process 500 may include additional implementations, such as any single implementation or any combination of implementations described below and/or in connection with one or more other processes described elsewhere herein.

In some implementations, the data model may be trained using a means square error (MSE) function that is part of a cost function and that accounts for a degree to which a probability value matches a ground truth value that represents an actual boundary position of a boundary. In some implementations, when determining the initial set of boundary positions, the image processing platform may use a soft argmax function of the data model to analyze a boundary map of the set of boundary maps, where the initial set of boundary positions include a boundary position for one or more y-coordinates of the set of y-coordinates of the 2-D image.

In some implementations, when determining the final set of boundary positions, the image processing platform may use the topological order identification technique to determine the final set of boundary positions in a manner to prevent the boundaries from overlapping with each other. In some implementations, the data model may be a convolutional neural network (CNN) and the topological order identification technique is trained using a rectifier that is a final output of the CNN.

In some implementations, when determining the final set of boundary positions, the image processing platform may identify a first position of a first voxel of the voxels that is associated with a first boundary, and may identify a second position of a second voxel of the voxels that is associated with a second boundary positioned in an expected position with respect to the first boundary, where the first voxel and the second voxel share a particular y-coordinate of the set of y-coordinates. Additionally, the image processing platform may determine, by comparing the first position and the second position, that the second position is positioned is not in the expected position with respect to the first position, and may modify the first position or the second position in a manner that allows the first position to be positioned in the expected position.

In some implementations, the device may be a first device, and the one or more actions may include one or more of: a first set of one or more actions to cause a result of whether the thickness levels of the layers are indicative of the disease to be displayed on an interface of a second device associated with a medical professional, a second set of one or more actions to cause medical equipment to perform a procedure on a patient, a third set of one or more actions to cause a prescription to be ordered for the patient, or a fourth set of one or more actions to cause a third device associated with the patient to be provided with a report that indicates the result of whether the thickness levels of the layers are indicative of the disease.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
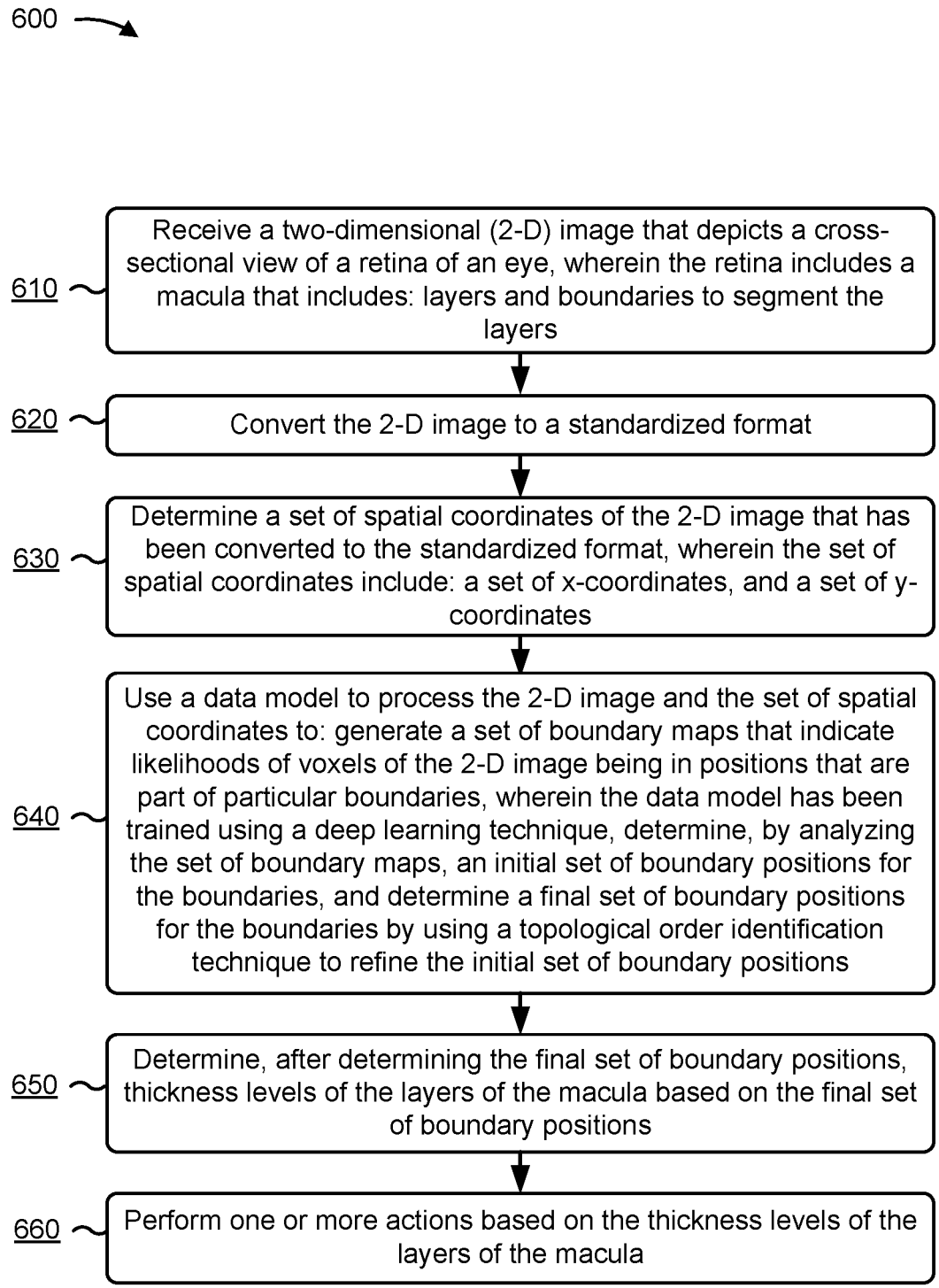

FIG. 6 is a flow chart of an example process 600 for determining boundary positions of boundaries that are used to segment layers of a macula by using a neural network to analyze a set of images that depict a cross-sectional view of the macula. In some implementations, one or more process blocks of FIG. 6 may be performed by an image processing platform (e.g., image processing platform 230). In some implementations, one or more process blocks of FIG. 6 may be performed by another device or a group of devices separate from or including the image processing platform, such as an imaging system (e.g., imaging system 210), a data storage device (e.g., data storage device 220), a user device (e.g., user device 250), and/or the like.

As shown in FIG. 6, process 600 may include receiving a two-dimensional (2-D) image that depicts a cross-sectional view of a retina of an eye, wherein the retina includes a macula that includes: layers, and boundaries to segment the layers (block 610). For example, the image processing platform (e.g., using computing resource 235, processor 320, memory 330, storage component 340, input component 350, communication interface 370, and/or the like) may receive a two-dimensional (2-D) image that depicts a cross-sectional view of a retina of an eye, as described above. In some implementations, the retina may include a macula that includes: layers, and boundaries to segment the layers.

As further shown in FIG. 6, process 600 may include converting the 2-D image to a standardized format (block 620). For example, the image processing platform (e.g., using computing resource 235, processor 320, memory 330, storage component 340, and/or the like) may convert the 2-D image to a standardized format, as described above.

As further shown in FIG. 6, process 600 may include determining a set of spatial coordinates of the 2-D image that has been converted to the standardized format, wherein the set of spatial coordinates include: a set of x-coordinates, and a set of y-coordinates (block 630). For example, the image processing platform (e.g., using computing resource 235, processor 320, memory 330, storage component 340, and/or the like) may determine a set of spatial coordinates of the 2-D image that has been converted to the standardized format, as described above. In some implementations, the set of spatial coordinates may include a set of x-coordinates, and a set of y-coordinates.

As further shown in FIG. 6, process 600 may include using a data model to process the 2-D image and the set of spatial coordinates to: generate a set of boundary maps that indicate likelihoods of voxels of the 2-D image being in positions that are part of particular boundaries, wherein the data model has been trained using a deep learning technique, determine, by analyzing the set of boundary maps, an initial set of boundary positions for the boundaries, and determine a final set of boundary positions for the boundaries by using a topological order identification technique to refine the initial set of boundary positions (block 640). For example, the image processing platform (e.g., using computing resource 235, processor 320, memory 330, storage component 340, and/or the like) may use a data model to process the 2-D image and the set of spatial coordinates to generate a set of boundary maps that indicate likelihoods of voxels of the 2-D image being in positions that are part of particular boundaries, to determine, by analyzing the set of boundary maps, an initial set of boundary positions for the boundaries, and to determine a final set of boundary positions for the boundaries by using a topological order identification technique to refine the initial set of boundary positions, as described above. In some implementations, the data model has been trained using a deep learning technique.

As further shown in FIG. 6, process 600 may include determining, after determining the final set of boundary positions, thickness levels of the layers of the macula based on the final set of boundary positions (block 650). For example, the image processing platform (e.g., using computing resource 235, processor 320, memory 330, storage component 340, and/or the like) may determine, after determining the final set of boundary positions, thickness levels of the layers of the macula based on the final set of boundary positions, as described above.

As further shown in FIG. 6, process 600 may include performing one or more actions based on the thickness levels of the layers of the macula (block 660). For example, the image processing platform (e.g., using computing resource 235, processor 320, memory 330, storage component 340, input component 350, communication interface 370, and/or the like) may perform one or more actions based on the thickness levels of the layers of the macula, as described above.

Process 600 may include additional implementations, such as any single implementation or any combination of implementations described below and/or in connection with one or more other processes described elsewhere herein.

In some implementations, a likelihood that a voxel of the voxels is in a position that is part of a particular boundary may be relative to other voxels of the voxels that share a y-coordinate of the set of y-coordinates with the voxel. In some implementations, the image processing platform may train the data model using a cost function that accounts for a degree to which a probability value of the data model matches a ground truth value that represents an actual boundary position of a boundary.

In some implementations, when using the data model to determine the initial set of boundary positions, the image processing platform may use a soft argmax function of the data model to analyze a boundary map of the set of boundary maps, where the initial set of boundary positions include a boundary position for a y-coordinate of the set of y-coordinates of the 2-D image. In some implementations, when determining the final set of boundary positions, the image processing platform may use the topological order identification technique to determine the final set of boundary positions in a manner to prevent the boundaries from overlapping with each other.

In some implementations, when using the data model to determine the final set of boundary positions, the image processing platform may identify a first position of a first voxel of the voxels that is associated with a first boundary, and may identify a second position of a second voxel of the voxels that is associated with a second boundary in an expected position with respect to the first boundary, where the first voxel and the second voxel share a particular y-coordinate of the set of y-coordinates. Additionally, the image processing platform may determine, by comparing the first position and the second position, that the second position is not in the expected position with respect to the first position, and may modify the first position or the second position in a manner that allows the first position to be positioned in the expected position.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

Some implementations are described herein in connection with thresholds. As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

Certain user interfaces have been described herein and/or shown in the figures. A user interface may include a graphical user interface, a non-graphical user interface, a text-based user interface, and/or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method, comprising:
   receiving, by a device, a two-dimensional (2-D) image that depicts a cross-sectional view of a retina of an eye,
      wherein the retina includes a macula that includes:
         layers, and
         boundaries that are used to segment the layers;
   converting, by the device, the 2-D image to a standardized format;
   determining, by the device, a set of spatial coordinates of the 2-D image that is in the standardized format,
      wherein the set of spatial coordinates include:
         a set of x-coordinates,
         a set of y-coordinates, and
         wherein an area defined by the set of spatial coordinates includes a set of rows and a set of columns;
   generating, by the device and by using a data model to process the 2-D image and the set of spatial coordinates, a set of boundary maps that indicate likelihoods of voxels of the 2-D image being in positions that are part of particular boundaries,
      wherein the data model has been trained using a deep-learning technique, and
      wherein a likelihood that a voxel, of the voxels of the 2-D image, is in a position that is part of a particular boundary, is relative to other voxels, of the voxels of the 2-D image, that share a column of the set of columns;
   determining, by the device and by using the data model to analyze the set of boundary maps, an initial set of boundary positions for the boundaries;
   determining, by the device, a final set of boundary positions by using a topological order identification technique of the data model to refine the initial set of boundary positions; and
   providing, by the device, data that identifies the final set of boundary positions for display via an interface.

2. The method of claim 1, wherein the data model is trained using a cost function that accounts for a degree to which a probability value matches a ground truth value that represents an actual boundary position of a boundary of the boundaries.

3. The method of claim 1, wherein determining the initial set of boundary positions comprises:
   using a soft argmax function of the data model to analyze a boundary map of the set of boundary maps,
      wherein the initial set of boundary positions include a boundary position for each y-coordinate of the set of y-coordinates, and
      wherein the soft argmax function is fully differentiable with respect to each variable input to the soft argmax function.

4. The method of claim 1, wherein determining the final set of boundary positions comprises:
   using the topological order identification technique to determine the final set of boundary positions in a manner to prevent the boundaries from overlapping with each other.

5. The method of claim 1, wherein the data model is a convolutional neural network (CNN) and the topological order identification technique utilizes one or more rectifiers and is a final output layer of the CNN.

6. The method of claim 1, wherein determining the final set of boundary positions comprises:
   identifying a first position of a first voxel, of the voxels of the 2-D image, that is associated with a first boundary,
   identifying a second position of a second voxel, of the voxels of the 2-D image, that is associated with a second boundary that is in an expected position relative to the first boundary,
      wherein the first voxel and the second voxel share a particular y-coordinate of the set of y-coordinates,
   determining, by comparing the first position and the second position, that the second position is not in the expected position relative to the first position, and
   modifying the second position in a manner that allows the second position to be positioned in the expected position.

7. The method of claim 1, further comprising:
   determining, after determining the final set of boundary positions, thickness levels of the layers of the macula based on the final set of boundary positions; and
   determining whether the thickness levels of the layers are indicative of a disease; and
   wherein providing the data that identifies the final set of boundary positions for display via the interface comprises:
      providing, for display via the interface, an indication of whether the thickness levels of the layers are indicative of the disease.

8. A device, comprising:
   one or more memories; and
   one or more processors, operatively coupled to the one or more memories, configured to:
      identify a data model that is trained using deep learning to determine likelihoods of particular voxels being within a layer of a particular macula;
      receive a two-dimensional (2-D) image that depicts a cross-sectional view of a macula of an eye,
         wherein the macula includes:
            layers, and
            boundaries to segment the layers;
      determine a set of spatial coordinates of the 2-D image,
         wherein the set of spatial coordinates include:
            a set of x-coordinates, and
            set of y-coordinates;
      generate, by using the data model to process the 2-D image and the set of spatial coordinates, a set of boundary maps that indicate likelihoods of voxels of the 2-D image being in positions that are part of particular boundaries,
         wherein a likelihood that a voxel, of the voxels of the 2-D image, is in a position that is part of a particular boundary is relative to other voxels, of the voxels of the 2-D image, that share a y-coordinate of the set of y-coordinates with the voxel;

determine, by using the data model to analyze the set of boundary maps, an initial set of boundary positions for the boundaries;
determine a final set of boundary positions by using a topological order identification technique of the data model to refine the initial set of boundary positions;
determine, after determining the final set of boundary positions, thickness levels of the layers of the macula based on the final set of boundary positions;
determine whether the thickness levels of the layers are indicative of a disease; and
perform one or more actions based on determining whether the thickness levels of the layers are indicative of the disease.

9. The device of claim 8, wherein the data model is trained using a custom cost function that utilizes smooth L1 loss and that accounts for a degree of similarity between predicted boundary positions and ground truth boundary positions.

10. The device of claim 8, wherein the one or more processors, when determining the initial set of boundary positions, are to:
use a soft argmax function of the data model to analyze a boundary map of the set of boundary maps,
wherein the initial set of boundary positions include a boundary position for one or more y-coordinates of the set of y-coordinates of the 2-D image.

11. The device of claim 8, wherein the one or more processors, when determining the final set of boundary positions, are to:
use the topological order identification technique to determine the final set of boundary positions in a manner to prevent the boundaries from overlapping with each other.

12. The device of claim 8, wherein the data model is a convolutional neural network (CNN) and the topological order identification technique is trained using a rectifier that is a final output of the CNN.

13. The device of claim 8, wherein the one or more processors, when determining the final set of boundary positions, are to:
identify a first position of a first voxel of the voxels that is associated with a first boundary,
identify a second position of a second voxel of the voxels that is associated with a second boundary positioned in an expected position with respect to the first boundary,
wherein the first voxel and the second voxel share a particular y-coordinate of the set of y-coordinates,
determine, by comparing the first position and the second position, that the second position is not in the expected position with respect to the first position, and
modify the second position in a manner that allows the second position to be positioned in the expected position.

14. The device of claim 8, wherein the device is a first device;
wherein the one or more actions include one or more of:
a first set of one or more actions to cause a result of whether the thickness levels of the layers are indicative of the disease to be displayed on an interface of a second device associated with a medical professional,
a second set of one or more actions to cause medical equipment to perform a procedure on a patient,
a third set of one or more actions to cause a prescription to be ordered for the patient, or
a fourth set of one or more actions to cause a third device associated with the patient to be provided with a report that indicates the result of whether the thickness levels of the layers are indicative of the disease.

15. A non-transitory computer-readable medium storing instructions, the instructions comprising:
one or more instructions that, when executed by one or more processors of a device, cause the one or more processors to:
receive a two-dimensional (2-D) image that depicts a cross-sectional view of a retina of an eye,
wherein the retina includes a macula that includes:
layers, and
boundaries to segment the layers;
convert the 2-D image to a standardized format;
determine a set of spatial coordinates of the 2-D image that has been converted to the standardized format,
wherein the set of spatial coordinates include:
a set of x-coordinates, and
a set of y-coordinates;
use a data model to process the 2-D image and the set of spatial coordinates to:
generate a set of boundary maps that indicate likelihoods of voxels of the 2-D image being in positions that are part of particular boundaries,
wherein a likelihood that a voxel, of the voxels of the 2-D image, is in -a position that is part of a particular boundary, is relative to other voxels, of the voxels of the 2-D image, that share a y-coordinate of the set of y-coordinates with the voxel, and
wherein the data model has been trained using a deep learning technique;
determine, by analyzing the set of boundary maps, an initial set of boundary positions for the boundaries, and
determine a final set of boundary positions for the boundaries by using a topological order identification technique to refine the initial set of boundary positions;
determine, after determining the final set of boundary positions, thickness levels of the layers of the macula based on the final set of boundary positions; and
perform one or more actions based on the thickness levels of the layers of the macula.

16. The non-transitory computer-readable medium of claim 15, wherein the one or more instructions, when executed by the one or more processors, further cause the one or more processors to:
train the data model using a cost function that accounts for a degree to which a probability value of the data model matches a ground truth value that represents an actual boundary position of a boundary.

17. The non-transitory computer-readable medium of claim 15, wherein the one or more instructions, that cause the one or more processors to use the data model to determine the initial set of boundary positions, cause the one or more processors to:
use a soft argmax function of the data model to analyze a boundary map of the set of boundary maps,
wherein the initial set of boundary positions include a boundary position for a y-coordinate of the set of y-coordinates of the 2-D image.

18. The non-transitory computer-readable medium of claim 15, wherein the one or more instructions, that cause the one or more processors to determine the final set of boundary positions, cause the one or more processors to:

use the topological order identification technique to determine the final set of boundary positions in a manner to prevent the boundaries from overlapping with each other.

19. The non-transitory computer-readable medium of claim 15, wherein the one or more instructions, that cause the one or more processors to use the data model to determine the final set of boundary positions, cause the one or more processors to:
   identify a first position of a first voxel of the voxels that is associated with a first boundary,
   identify a second position of a second voxel of the voxels that is associated with a second boundary in an expected position with respect to the first boundary, wherein the first voxel and the second voxel share a particular y-coordinate of the set of y-coordinates,
   determine, by comparing the first position and the second position, that the second position is not in the expected position with respect to the first position, and
   modify the second position in a manner that allows the second position to be positioned in the expected position.

20. The non-transitory computer-readable medium of claim 15, wherein the one or more instructions further cause the one or more processors to:
   determine whether the thickness levels of the layers are indicative of a disease.

\* \* \* \* \*